United States Patent [19]

Haviv et al.

[11] 4,093,804
[45] June 6, 1978

[54] PYRIDINIUMMETHYLARYL-SUBSTITUTED CEPHALOSPORIN DERIVATIVES

[75] Inventors: Fortuna Haviv, Montreal, Canada; Abraham Patchornik, Ness-Ziona, Israel

[73] Assignee: Yeda Research and Development Co., Ltd., Rehovot, Israel

[21] Appl. No.: 759,466

[22] Filed: Jan. 14, 1977

Related U.S. Application Data

[62] Division of Ser. No. 625,570, Oct. 24, 1975, Pat. No. 4,026,887.

[51] Int. Cl.$^2$ ............................................ C07D 501/36

[52] U.S. Cl. .................................... 544/27; 424/246; 544/21; 544/26
[58] Field of Search ................ 260/243 C; 544/26, 27

[56]  References Cited

U.S. PATENT DOCUMENTS

| | | | |
|---|---|---|---|
| 4,024,249 | 5/1977 | Müller et al. | 260/243 C |
| 4,026,887 | 5/1977 | Haviv et al. | 260/243 C |

*Primary Examiner*—Nicholas S. Rizzo
*Attorney, Agent, or Firm*—L. Ruth Hattan; Eugene O. Retter; George W. Rauchfuss, Jr.

[57]  ABSTRACT

Novel cephalosporin antibiotic derivatives.

36 Claims, No Drawings

PYRIDINIUMMETHYLARYL-SUBSTITUTED CEPHALOSPORIN DERIVATIVES

This is a division of application Ser. No. 625,570, filed Oct. 24, 1975, now U.S. Pat. No. 4,026,887, issued May 31. 1977.

FIELD OF INVENTION

This invention relates to novel cephalosporin derivatives useful as antibiotics and processes for their preparation.

SUMMARY OF INVENTION

Compounds of the following general Formula I are useful as antibiotic agents:

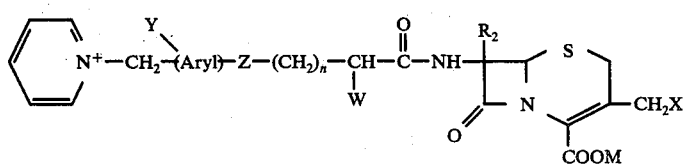

Formula I wherein Aryl is selected from phenyl and 2-thienyl; Y is selected from hydrogen, chlorine, bromine, a straight or branched lower alkyl group of from 1 to 4 carbon atoms, and a lower alkoxy group of from 1 to 4 carbon atoms with the proviso that when Aryl is 2-thienyl, Y is hydrogen; Z is selected from a bond, oxygen, sulfur and imino with the proviso that when Aryl is 2-thienyl, Z is a bond; W is selected from hydrogen, methyl, amino, hydroxy, $SO_3H$ and $COOR_1$ wherein $R_1$ is selected from hydrogen and 5-indanyl; $n$ is zero, 1 or 2 with the proviso that when W is other than hydrogen or methyl, and Z is other than a bond, $n$ is not zero; $R_2$ is selected from hydrogen or methoxy; M is selected from an anion; hydrogen; alkanoyloxymethyl wherein the alkanoyl moiety contains from 1 to 5 carbon atoms and may be straight or branched; alkanoylaminomethyl wherein the alkanoyl moiety contains from 1 to 5 carbon atoms and may be straight or branched and wherein the amino nitrogen may be substituted with an alkyl group of from 1 to 4 carbon atoms; alkoxycarbonylaminomethyl wherein the alkoxy moiety contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; or aminoalkanoyloxymethyl wherein the alkanoyl moiety contains from 2 to 15 carbon atoms, and the amino nitrogen atom may be mono- or di-substituted with a lower alkyl group of from 1 to 4 carbon atoms; with the proviso that when M is other than an anion, the compounds exist in the form of a salt of a pharmaceutically acceptable inorganic or organic acid; X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio and 1,2,3-triazol-5-ylthio; and pharmaceutically acceptable salts and individual optical isomers thereof. Compounds wherein M is an anion are also known as inner salts or zwitterions.

DETAILED DESCRIPTION OF INVENTION

In general Formula I the substituent group is represented by M in addition to being hydrogen or an anion may also be alkanoyloxymethyl as represented by the structure:

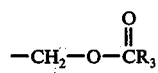

wherein $R_3$ is selected from a straight or branched lower alkyl group of from 1 to 4 carbon atoms; alkanoylaminomethyl or alkoxycarbonylaminomethyl as represented by the structure:

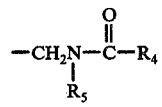

wherein $R_4$ represents a straight or branched lower alkyl group of from 1 to 4 carbon atoms or a straight or branched alkoxy group of from 1 to 4 carbon atoms, and $R_5$ is selected from hydrogen and a lower alkyl group of from 1 to 4 carbon atoms; p-(alkanoyloxy)benzyl as represented by the structure:

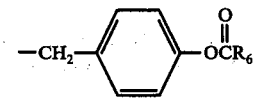

wherein $R_6$ is a straight or branched lower alkyl of from 1 to 4 carbon atoms; and aminoalkanoyloxymethyl as represented by the group:

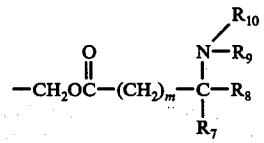

wherein $m$ is 0 to 5, each of $R_7$ and $R_8$ is selected from hydrogen or lower alkyl of from 1 to 4 carbon atoms, and each of $R_9$ and $R_{10}$ is selected from hydrogen or a straight or branched lower alkyl group of from 1 to 4 carbon atoms.

Illustrative examples of straight or branched lower alkyl groups of from 1 to 4 carbon atoms which Y, $R_3$, $R_4$, $R_6$, $R_9$ and $R_{10}$ may represent are methyl, ethyl, N-propyl, isopropyl, n-butyl and tert-butyl.

Examples of lower alkyl groups of from 1 to 4 carbon atoms which $R_5$, $R_7$, and $R_8$ may represent are methyl, ethyl, n-propyl and n-butyl.

Examples of lower alkoxy groups which Y may represent are methoxy, ethoxy, n-propoxy and n-butoxy.

In general Formula I, the substituent group X may represent in addition to hydrogen or acetoxy, a heterocyclicthio group selected from 1,3,4thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol- 5-ylthio, 2-methyl-1,3,4-thiadiazol-5-ylthio, or 1,2,3triazol-5-ylthio as represented by the following respective structures:

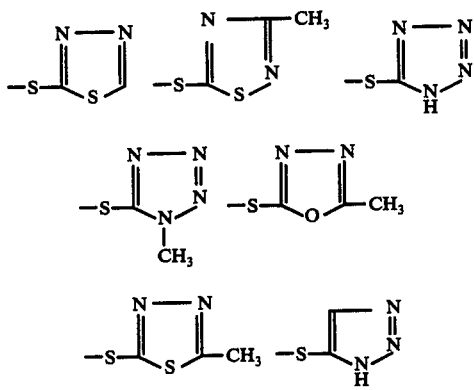

When the Aryl group in the compounds of general Formula I represent phenyl, each of the pyridiniummethyl substituent and the Y substituent may be individually attached to any of the positions 2 through 6 of the phenyl ring. Compounds of this type may be represented by the following general Formula II.

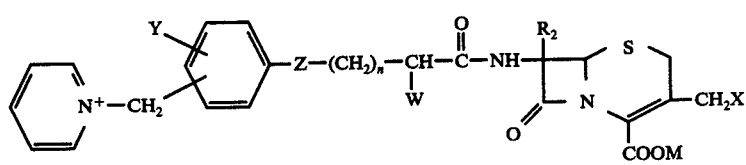

Formula II

In the above Formula II, the substituent groups Y, Z, n, W, $R_2$, M and X have the meanings defined in general Formula I.

The preferred positions of the attachment of the pyridiniummethyl substituent in the above Formula II are the ortho- and para-positions of the phenyl ring.

When the Aryl group in the compounds of general Formula I represents 2-thienyl, Y is hydrogen and Z is a bond. Compounds of this type may be represented by the following Formula III.

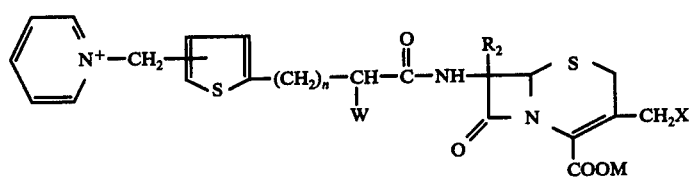

Formula III

In the compounds of the above Formula III, the pyridiniummethyl substituent may be attached at the 4 or 5 positions of the thienyl group. In the above Formula III, the substituents as represented by n, W, $R_2$, M and X have the meanings defined in general Formula I.

In the compounds of general Formulas I to III, it is apparent that the $R_2$ substituent may be either cis or trans to the hydrogen atom at the 6-position of the cephalosporin derivatives. The compounds of Formulas I to III wherein the $R_2$ substituent is cis to the aforementioned hydrogen atom are preferred.

Other preferred embodiments of this invention are:
A. compounds wherein W represents hydrogen, hydroxy, amino, $SO_3H$ and $COOR_1$ wherein $R_1$ represents hydrogen in that such substitution results in compounds having broader spectrum activity and/or improved oral activity for example wherein:
  1. W represents hydroxy are more resistant to β-lactamase organisms;
  2. W represents $SO_3H$ or $COOR_1$ represents hydrogen have broader gram negative spectrum;
  3. W represents $NH_2$ have improved oral activities;
B. compounds wherein $R_2$ represents methoxy are of particular interest in that such compounds demonstrate antibacterial activity against cephalosporinase producing gram negative organisms.
C. compounds wherein X represents acetoxy, 2-methyl-1,3,4-thiadiazol-5-ylthio, or 1-methyltetrazol-5-ylthio. Of the preferred embodiments set forth in (A), (B) and (C) compounds wherein Z represents a bond are more preferred. The most preferred compounds of this invention are those represented by the following Formula IV:

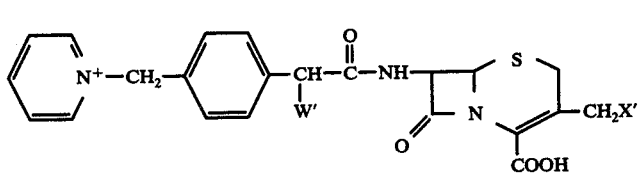

Formula IV wherein W' is selected from hydrogen, hydroxy, amino, COOH or $SO_3H$; X' is selected from hydrogen, acetoxy, 2-methyl-1,3,4-thiadiazol-5-ylthio or 1-methyltetrazol-5-ylthio; and pharmaceutically acceptable salts thereof.

In the above Formula IV, compounds wherein the hydrogen atoms at the 6- and 7-positions are cis to one another are preferred.

The individual optical isomers of the compounds of this invention wherein W or W' is other than hydrogen are also included within the scope of this invention.

The non-toxic inorganic acid addition salts of the compounds of this invention such as mineral acid addition salts, for example, hydrogen chloride, hydrogen bromide, hydrogen iodide, sulfates, sulfamate, phosphate, and organic acid addition salts, for example, maleate, acetate, citrate, oxalate, succinate, benzoate, tartrate fumarate, malate, mandalate, and ascorbate, are also included within the scope of this invention.

Also within the scope of this invention are the nontoxic pharmaceutically acceptable salts of the compounds of this invention wherein W represents COOH or $SO_3H$ and compounds wherein M represents hydrogen. Illustrative pharmaceutically acceptable salts of these acids derivatives are primary, secondary, or tertiary amines, for example, cyclohexylamine, ethylamine, and pyridine.

The pharmaceutically acceptable cations which may be present as the group M in the compounds of general Formulas I to III include alkali metal ion, for example, sodium ion, potassium ion, calcium ion as well as ammonium, an organic amine cation, for example, lower alkyl ammonium groups, such as triethylammonium, and N-ethyl piperidine.

The salt forms of compounds of Formulas I to III wherein M is a pharmaceutically acceptable cation are prepared in the manner recognized in the art and may be found in situ or by reacting the corresponding acid with base, for example, sodium bicarbonate or triethylamine.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds, and mammals, for example, cats, dogs, cows, sheep and horses, and humans. For oral administration, the compounds may be administered in the form of tablets, capsules or pills or in the form of elixirs or suspensions. For parenteral administration, they may best be used in the form of a sterile aqueous aolution which may contain other solutes, for example, enough saline or glucose to make the solution isotonic. For topical administration, the compounds may be incorporated in creams or ointments.

Illustrative examples of bacteria against which the compounds of this invention are active are *Staphylococcus aureus, Salmonella schottmuelleri, Klebsiella pneumoniae, Diplococcus pneumoniae,* and *Streptococcus pyogenes.*

An illustrative example of a cephalosporin derivative of this invention is 3-[(acetyloxy)methyl]-7-[[2-[4-(pyridiniummethyl)phenyl]acetyl]amino]-8-oxo-5-thia-1-azabicyclo-[4.2.0]oct-2-ene-2-carboxylic acid. Additional examples of compounds of this invention are set forth hereinbelow in the specific examples which are representative of the invention.

The compounds of this invention wherein $R_1$ is hydrogen are prepared by coupling 7-aninocephalosporanic acid or a derivative thereof having the formula:

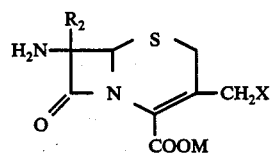

Formula V wherein $R_2$, M and X have the meaning defined in general Formula I with an acid of the following Formula VI or a functional derivative thereof:

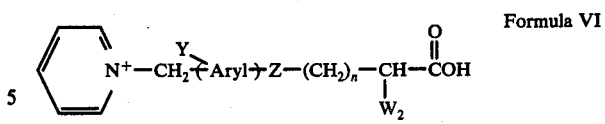

Formula VI wherein Aryl, Y, Z and n have the meanings defined in general Formula I, and $W_2$ is selected from hydrogen, methyl, amino, hydroxy, $SO_3H$, or COOH. When the substituted group $W_2$ in the above Formula VI represents an amino group, suitable blocking groups, for example, an acid salt such as hydrochloride salt, an acyl group, or tert-butoxycarbonyl may be employed to protect the amino function. Such blocking groups are removed after the coupling reaction by the methods generally known in the art, for example, as described by Lemiuex et al., in U.S. Pat. No. 3,657,232.

Functional equivalents of the acids as represented by Formula VI include the acid halide, for example, the acid chloride, acid anhydrides, including mixed anhydrides with, for example, alkylphosphoric acids, lower aliphatic mono esters of carbonic acid, or alkyl or aryl sulphonic acids. Additonally, the acid azide or an active ester or thioester for example, with p-nitrophenol, 2,4-dinitrophenol, or thioacetic acid, may be used or the free acid as represented by Formula VI may be coupled with the 7-aminocephalosporanic acid derivative as represented by Formula V after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide. Just as the final products of this invention must exist in a form to satisfy the positive charge on the pyridinium group so must the compounds of Formula VI, for example, in the form of a salt of a pharmaceutically acceptable inorganic or organic acid.

The coupling reaction is generally carried out in the presence of a solvent. Suitable solvents include ethyl acetate, acetone, dioxane, acetonitrile, chloroform, ethylene chloride, tetrahydrofuran and dimethylformamide. As hydrophilic solvents are employed, mixtures of these solvents with water are also suitable for the above reactions. The coupling reaction is generally carried out in the presence of a base, for example, an alkaline bicarbonate. The temperature of the reaction may vary from −10° to 100° C, and the reaction time may vary from about ½ hour to 10 hours. The cephalosporin products are isolated by conventional methods.

Compounds of Formula V wherein $R_2$ is hydrogen, M is hydrogen, or an anion and X is hydrogen or acetoxy are commercially available or may be prepared by the methods well-known in the art. The corresponding compounds wherein $R_2$ is methoxy may be prepared by the general procedures described in U.S. Pat. No. 3,778,432.

Compounds of Formula V wherein M is alkanoyloxymethyl may be prepared by reacting the corresponding acid in the form of a salt, such as, an alkali metal salt or the triethylammonium salt with a compound of formula:

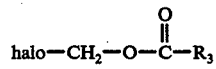

wherein halo is chlorine or bromine, and $R_3$ is a straight or branched lower alkyl group of from 1 to 4 carbon atoms, by the general procedure described in U.S. Pat. No. 3,655,658.

Compounds of Formula V wherein M is alkanoylaminoethyl or alkoxycarbonylaminomethyl are prepared by treating the sodium salt of acid derivatives of Formula V in an organic solvent such as dimethylformamide or hexamethylphosphoramide, at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of Formula V wherein M is p-(alkanoyloxy)benzyl are prepared by adding two equivalents of the p-(alkanoyloxy)benzyl alcohol to a suspension of sodium salts of acid derivatives of Formula V and dimethylformamide or hexamethylphosphoramide after which the mixture is cooled to 0° C. 1.2 equivalents of dicyclohexylcarbodiimide and dimethylformamide are added dropwise to the mixture with stirring. The mixture is sitrred at 0° C for ½ to 3 hours and then an additional 2 to 5 hours at room temperature. The formed dicyclohexylurea is removed by filtration and the filtrate is diluted with chloroform, methylene chloride or ethylacetate, washed with water and dried to give the product.

Compounds of Formula V wherein M is aminoalkanoyloxymethyl are prepared by mixing a suspension of the sodium salt of an acid of Formula V and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride washed with water, aqueous base, then water. The organic phase is separated and the precipitate isolated by conventional means followed by deprotection of the amine group to give the product.

Compounds of Formula V wherein X is a heterocyclic thio group as described in Formula I are prepared by dissolving 1 equivalent of the acid in the form of a salt, such as, the sodium salt wherein X is acetoxy in about 500 to 2000 ml of water at a temperature of from 50° to 80° C under a nitrogen atmosphere and subsequently adding 1 equivalent of a base, such as, triethylammonium or sodium bicarbonate and 1 to 3 equivalents of an appropriate heterocyclicthiol selected from a compound having the following structure:

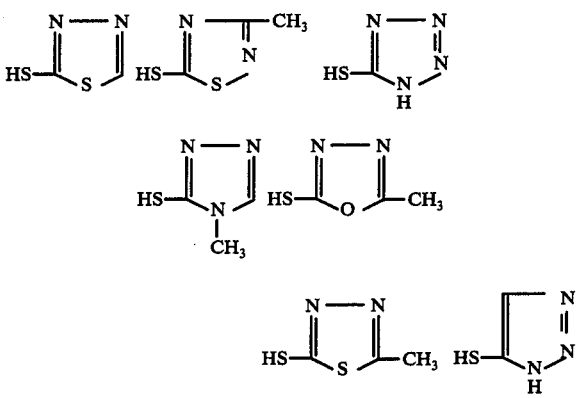

The reaction mixture is stirred at 50° to 90° C for about 2 to 6 hours after which the water is evaporated, and the residue is taken up in an organic solvent, such as, methanol, ethanol, or dimethylformamide, and precipitated with an organic solvent, such as, acetonitrile, acetone, ethylacetate or chloroform.

Compounds of general Formula VI are prepared by treating a compound of the formula:

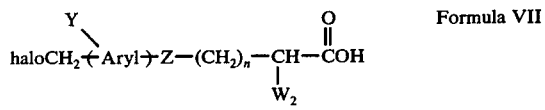

Formula VII wherein halo is chlorine or bromine, and Aryl, Y, Z, n and $W_2$ have the meanings defined in general Formula VI with pyridine in a solvent, such as, a lower alcohol, for example, methanol, ethanol, isopropyl alcohol or n-butanol or dimethylsulphoxide, dimethylformamide or aqueous mixture of these solvents, for from ½ hour to 24 hours at a temperature range from 0° to 125° C. The products can be isolated by conventional procedures. In some instances, it may be more convenient to convert the acid as represented by Formula VII to the corresponding methyl ester by, for example, treating the acid with diazomethane at −10° C then stirring the mixture for about 10 to 30 minutes at room temperature.

When the substituent group $W_2$ in compounds of general Formula VII represents amino, the amino group is protected by a suitable blocking group, for example, tert-butoxycarbonyl prior to the treatment with pyridine. The blocking group may be removed after the coupling reaction by a mild acid hydrolysis or hydrogenolysis by procedures known in the art.

The compounds of Formula VII are prepared by direct halomethylation as described hereinbelow of an acid of the formula:

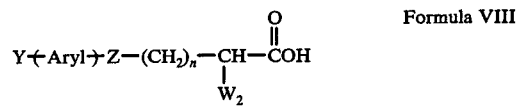

Formula VIII wherein Aryl, Y, Z, n and $W_2$ have the meanings defined in general Formula VI which are commercially available or are obtained by methods well-known in the art.

When the substituent group $W_2$ in the compound of Formula VIII represents amino, the amino group is protected by a suitable blocking group as for example described hereinabove in reference to compounds of general Formula VII.

The halomethylated derivatives of the compounds of Formula VIII are obtained by several methods. For example, the compound of Formula VIII with a source of formaldehyde such as paraformaldehyde, $ClCH_2OCH_3$, or formaline solution in the presence of a Lewis acid, such as $ZnCl_2$, $AlCl_3$, $SnCl_4$ or $ClSO_3H$ in a solvent, such as petroleum ether, chloroform, carbontetrachloride or benzene, at a temperature ranging from −10° to 100° C during which time hydrogen chloride gas or hydrogen bromide gas is bubbled into the reaction mixture will give compounds of Formula VII.

Additionally, upon reaction of an acid of Formula VIII with trioxane in acetic acid or phosphoric acid at temperatures of from −10° to 100° C during which time hydrogen bromide or hydrogen chloride gas is bubbled through the reaction mixture, compounds of general Formula VII are obtained. Or, the reaction of an acid of Formula VIII in the presence of a Lewis acid, such as those described hereinabove, with chloromethyl ether at temperatures of from −10° to 100° C or the reaction of the acid in acetic acid or concentrated sulfuric acid with dichloromethyl ether in the presence of zinc chloride will give the compounds of general Formula VII.

The compounds of Formula VII wherein $W_2$ represents COOH, and Aryl is phenyl are preferably obtained by treating the corresponding diethyl ester of Formula VIII with 40% formaline in the presence of anhydrous zinc chloride in benzene at about 50° C during which time hydrogen chloride or hydrogen bromide gas is bubbled into the reaction mixture followed by acid hydrolysis.

Compounds of Formula VII wherein $W_2$ represents $SO_3H$ may be obtained by the halomethylation reactions described using an acid of Formula VIII wherein $W_2$ represent $SO_3H$ or the carboxymethyl ester thereof in which latter case the resulting halomethylated compound is converted to the free COOH by acid hydrolysis.

In the halomethylation of compounds of Formula VIII wherein $W_2$ represents OH it may be advantageous to protect the OH group prior to halomethylation as described by B. Reichert, et al., Pharmazie vol. 5, 10 (1950).

nitrophenol or hydroxysuccinimide groups with an acid of general Formula VI by the general procedure described in Canadian Pat. No. 892,580 issued Feb. 8, 1972, by substituting a compound of general Formula V for the penicillanic acid derivatives described therein.

Compounds of this invention wherein $R_1$ is hydrogen may also be prepared by solvolysis of a compound of the formula:

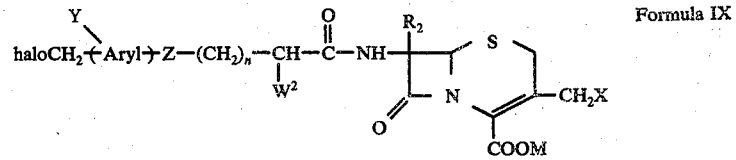

Formula IX wherein Aryl, Y, Z, n, $R_2$, M and X have the meanings defined in general Formula I; halo is chlorine or bromine; and $W^2$ is hydrogen, methyl, amino, hydroxy, $SO_3H$ or COOH; with pyridine in a solvent, such as, a lower alcohol, for example, methanol, ethanol, isopropyl alcohol, n-butanol or dimethylsulfoxide, dimethylformamide or aqueous mixtures of these solvents. The reaction is carried out from ½ hour to 24 hours at a temperature of from 0° to 125° C. The products are isolated by conventional means.

Additionally, the compounds of this invention wherein X represents a heterocyclic thio group selected from 1,3,4-thiadiazol-5-ylthio, 3-methyl-1,2,3,-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio or 1,2,3-triazol-5-ylthio and M represents hydrogen or an anion may be prepared by reacting the 3-[(acetyloxy)-methyl] derivative with the appropriate heterocyclic thiol group as represented by the following:

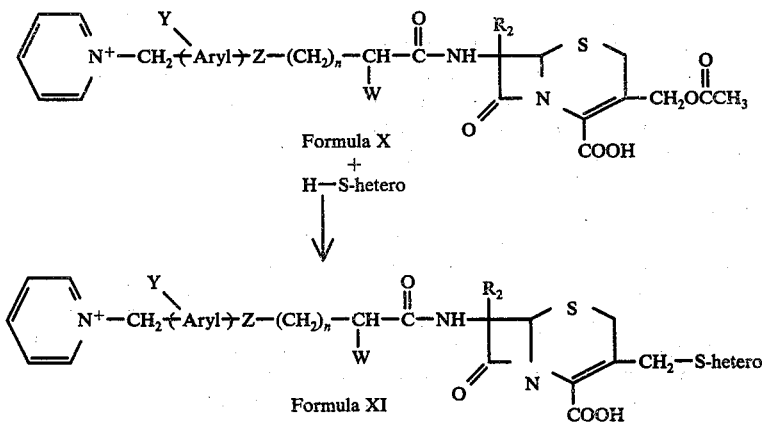

Compounds of this invention wherein $R_1$ is 5-indanyl are prepared by reacting the corresponding acid, that is, compounds of general Formula I wherein $R_1$ is hydrogen with 5-indanol in an inert solvent in the presence of N,N'-dicyclohexylcarbodiimide at pH of about 2.5 and a temperature of about 20° to 30° C. Equimolar amounts of the reactants are employed or a slight excess of the 5-indanyl may be used. The molar amount of N,N-dicyclohexylcarbodiimide employed is equivalent to the molar amount of 5-indanol. Suitable solvents for the reaction are dioxane, tetrahydrofuran, ethylacetate, dimethylformamide and methylene chloride.

The compounds of this invention may also be prepared by linking a modified polystyrene containing In the above Formulas X and XI the substituent groups Aryl, Y, Z, n, W and $R_2$ have the meanings defined in general Formula I, and the moiety S-hetero is selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5ylthio, 2-methyl-1,3,4-thiadiazol-5-ylthio or 1,2,3-triazol-5ylthio. In the above reaction when M is hydrogen resulting in a carboxy group at the 4-position of the cephalosporin ring the compounds exist in the form of a salt of a pharmaceutically acceptable inorganic or organic acid.

In the above reaction, one equivalent of an aqueous solution of a zwitterion at a pH range of 3.5 to 7.5, preferably 5.5 to 6.5, may be reacted with one equivalent of the heterothiol derivative to give compounds of Formula XI. This reaction can be carried out in about 2 to 6 hours at a temperature of from 25° to 90° C.

Compounds of this invention wherein M represents alkanoylaminomethyl or alkoxycarbonylaminomethyl, and W is other than COOH may also be prepared by reacting the corresponding compound wherein M is an anion with 1.5 to 2.5 equivalents of an appropriate alkanoylaminomethyl halide or alkoxycarbonylaminomethyl halide each of which may be represented by the structure:

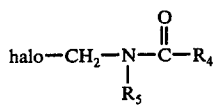

wherein halo is selected from a reactive halogen atom such as chlorine or bromine, $R_4$ is selected from a straight or branched lower alkyl group of from 1 to 4 carbon atoms or a straight or branched lower alkoxy group of from 1 to 4 carbon atoms, and $R_5$ is hydrogen or a lower alkyl group of from 1 to 4 carbon atoms. The reactants are stirred from about 1 to 5 hours in dimethylformamide, hexamethylphosphoramide or a similar solvent at a temperature ranging from 10° to 45° C after which the reaction mixture is poured into ice water and decanted. The oily residue is taken up in an organic solvent such as ethylacetate, methylene chloride or benzene washed with base and then with water and dried over magnesium sulfate. The organic solution is evaporated to dryness in vacuo to give the desired ester.

Prior to the above esterification reaction, compounds wherein W represents amino are protected with blocking groups for example tert-butoxycarbonyl or carbobenzyloxy, such groups being removed on completion of the esterification procedure by methods generally known in the art, for example, by methods set forth in the aforementioned U.S. Pat. No. 3,657,232.

Compounds of this invention wherein M represents p-(alkanoyloxy)benzyl and W is other than COOH may also be prepared by reacting molar equivalents of the corresponding acid and a p-(alkanoyloxy)benzyl alcohol wherein the alkanoyl moiety contains from 1 to 4 carbon atoms and may be straight or branched. The reactants are dissolved in an organic solvent such as dimethylformamide or hexamethylphosphoramide and cooled to a temperature of from −15° to 25° C after which an equivalent quantity of dicyclohexylcarbodiimide in dimethylformamide or hexamethylphosphoramide is added dropwise to the reaction mixture with stirring. Stirring is continued for ½ to 2 hours at temperatures of from −15° to 25° C and then 4 to 6 hours at from 25° to 45° C. The formed dicyclohexylurea is removed by filtration, and the filtrate is diluted with chloroform, ethylacetate or methylene chloride and washed with water. The organic layer is dried and evaporated to give the product.

Compounds of this invention wherein M is alkanoyloxymethyl, and W is other than COOH may also be prepared by reacting the corresponding compound wherein M is an anion with a compound of the formula:

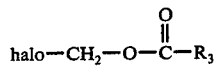

wherein halo is chlorine or bromine and $R_3$ is a straight or branched lower alkyl group of from 1 to 4 carbon atoms by the general procedure described in U.S. Pat. No. 3,655,658.

Compounds of this invention wherein M is aminoalkanoyloxymethyl, and W is other than COOH may be prepared by mixing a suspension of the corresponding compound wherein M is an anion and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride, washed with water, aqueous base, then water. The organic phase is separated and the precipitate isolated by conventional means followed by deprotection of the amine group to give the product.

The following specific examples are illustrative of the compounds of the invention and methods of preparation of the compounds.

EXAMPLE 1 p-Chloromethylphenylacetyl chloride (A) At a temperature of from −10° to 0° C hydrogen chloride gas is bubbled through a stirred mixture of 102 g of phenylacetic acid, 67.5 g of paraformaldehyde and 67.5 g of zinc chloride in 1000 ml of petroleum ether for one hour. Stirring is continued for about one hour at room temperature after which the mixture is refluxed for about 2 hours during which time hydrogen chloride gas is bubbled into the mixture. To the reaction mixture is added 1000 ml each of methylene chloride and water. The organic phase is separated and the aqueous phase is extracted twice with methylene chloride. The combined organic phase are extracted four times with a saturated sodium bicarbonate solution. The organic neutral phase is dried over anhydrous sodium sulfate, filtered and the solvent is removed under vacuum to give a neutral by-product which is further identified in Example 5 below. The basic aqueous phase is separated and acidified with cold concentrated hydrochloric acid to pH 2-3, then extracted three times with methylene chloride. The methylene chloride fraction is dried over anhydrous sodium sulfate, filtered and the solvent evaporated. The resulting oily acidic product is chromatographed on silica gel using benzene and benzene-acetone as the eluant to give p-chloromethylphenylacetic acid which is recrystallized from hot chloroform. M.P. 147°–149° C.

(B) A mixture of 1 g of p-chloromethylphenylacetic acid and 6 ml of thionyl chloride is stirred at room temperature for 25 hours after which the excess thionyl chloride is removed under vacuum to yield p-chloromethylphenylacetyl chloride.

When in Example 1 (A) an acid selected from Table I is substituted for phenylacetic acid the respective chloromethyl derivative listed in Table I is obtained which can be converted to the acid chloride by the procedure of Example 1 (B).

TABLE 1

| Acid | Chloromethyl derivative |
|---|---|
| hydrotropic acid | p-chloromethylhydrotro- |

TABLE 1-continued

| Acid | Chloromethyl derivative |
| --- | --- |
| mandelic acid | pic acid<br>p-chloromethylmandelic acid |
| dihydrocinnamic acid | p-chloromethyldihydrocinnamic acid |
| 2-methylhydrocinnamic acid | p-chloromethyl-2-methylhydrocinnamic acid |
| 3-phenyllactic acid | 3-(p-chloromethylphenyl)lactic acid |
| 4-phenylbutyric acid | 4-(p-chloromethylphenyl)butyric acid |
| 2-methyl-4-phenylbutyric acid | 2-methyl-4-(p-chloromethylphenyl)butyric acid |
| 2-hydroxy-4-phenylbutyric acid | 2-hydroxy-4-(p-chloromethylphenyl)butyric acid |
| phenoxyacetic acid | p-chloromethylphenoxyacetic acid |
| 2-phenoxypropionic acid | 2-(p-chloromethylphenoxy)propionic acid |
| 4-phenoxybutyric acid | 4-(p-chloromethylphenoxy)butyric acid |
| 2-methyl-4-phenoxybutyric acid | 2-methyl-4-(p-chloromethylphenoxy)butyric acid |
| 3-phenoxypropionic acid | 3-(p-chloromethylphenoxy)propionic acid |
| 3-phenoxylactic acid | 3-(p-chloromethylpenoxy)lactic acid |
| anilinoacetic acid | p-chloromethylanilino acetic acid |
| 2-hydroxy-2-(2-thienyl)acetic acid | 2-hydroxy-2-[2-(5-chloromethyl)thienyl]acetic acid |
| 2-anilinopropionic | 2-(p-chloromethyl)anilinopropionic acid |
| 4-anilinobutyric acid | 4-(p-chloromethylanilino)butyric acid |
| 3-anilinobutyric acid | 3-(p-chloromethylanilino)butyric acid |
| phenylthioacetic acid | p-chloromethylphenylthioacetic acid |
| 2-phenylthiopropionic acid | 2-(p-chloromethylphenyl)thiopropionic acid |
| 4-phenylthiobutyric acid | 4-(p-chloromethylphenyl)thiobutyric acid |
| o-chlorophenylacetic acid | o-chloro-p-chloromethylphenylacetic acid |

EXAMPLE 2 p-Chloromethylphenylglycine

A mixture of 2.03 g of trifluoroacetylated phenylglycine, 0.8 g of zinc chloride in chloromethylether is heated at 65° C for 12 hours. The excess reagent is removed under vacuum, and the residue is dissolved in $CH_2Cl_2$, washed with saturated $NaHCO_3$ solution then saturated sodium chloride solution. The neutral organic phase is dried over $Na_2SO_4$ and concentrated to an oil which was purified by column chromatography yielding the methyl ester of p-chlorophenylglycine which can be converted to the acid hydrochloride by hydrolysis with aqueous hydrochloric acid. The hydrochloride can be converted to the free base by adjusting the pH of the aqueous solution to about 5. Similarly, the chloromethyl derivatives listed in Table II may be prepared from the listed acid.

TABLE II

| Acid | Chloromethyl derivative |
| --- | --- |
| phenylalanine | p-(chloromethylphenyl)alanine |
| 2-amino-4-phenylbutyric acid | 2-amino-4-(p-chloromethylphenyl)butyric acid |
| 2-amino-4-phenoxybutyric acid | 2-amino-4-(p-chloromethylphenoxy)butyric acid |
| 3-phenoxyalanine | 3-(p-chloromethylphenoxy)alanine |
| 2-amino-4-anilinobutyric acid | 2-amino-4-(p-chloromethylanilino)butyric acid |
| 2-amino-4-phenylthiobutyric acid | 2-amino-4-(p-chloromethylphenyl)thiobutyric acid |

Table II-continued

| Acid | Chloromethyl derivative |
| --- | --- |
| 3-phenylthioalanine | 3-(p-chloromethylphenyl)thioalanine |
| 2-(2-thienyl)glycine | 2-[2-(5-chloromethyl)thienyl]glycine |
| 2-amino-3-(2-thienyl)propionic acid | 2-amino-3-[2-(5-chloromethyl)thienyl]propionic acid |
| 2-amino-4-(2-thienyl)butyric acid | 2-amino-4-[2-(5-chloromethyl)thienyl]butyric acid |

EXAMPLE 3 p-Chloromethylphenylmalonic acid

When in the procedure of Example 1 (A) an equivalent amount of phenylmalonic acid diethyl ester is substituted for phenylacetic acid, p-chloromethylphenylmalonic acid diethyl ester is obtained which yields the corresponding acid upon acid hydrolysis. In a similar manner the chloromethyl derivatives listed in Table III may be prepared when the diethyl ester of the corresponding acid listed in Table III is substituted for phenylmalonic acid diethyl ester.

TABLE III

| Acid | Chloromethyl derivative |
| --- | --- |
| 2-sulfophenylacetic acid | 2-sulfo-p-chloromethylphenylacetic acid |
| 3-phenyl-2-sulfopropionic acid | 3-(p-chloromethylphenyl)-2-sulfopropionic acid |
| 4-phenyl-2-sulfobutyric acid | 4-(p-chloromethylphenyl)-2-sulfobutyric acid |
| benzylmalonic acid | p-chloromethylbenzylmalonic acid |
| phenethylmalonic acid | p-chloromethylphenethylmalonic acid |
| 2-phenoxyethylmalonic acid | 2-(p-chloromethylphenoxy)ethylmalonic acid |
| 2-phenylthioethylmalonic acid | 2-(p-chloromethylphenyl)thioethylmalonic acid |
| anilinomethylmalonic acid | p-chloromethylanilinomethylmalonic acid |
| 2-thienylmalonic acid | 2-[2-(5-chloromethyl)thienyl]malonic acid |
| 2-thenylmalonic acid | 2-[2-(5-chloromethyl)thenyl]malonic acid |

EXAMPLE 4

5-Chloromethyl-2-thienylacetyl chloride

2-Thiophenecarboxylic acid is treated in a solution of chloroform with chloromethyl ether in the presence of 0.9 to 2.2 equivalents of aluminum chloride to give 5-chloromethyl-2-thienylcarboxylic acid. Treatment of the obtained acid with excess thionyl chloride at room temperature for about 16 hours yields the acid chloride which is reacted with diazomethane to give the corresponding diazoketone. A methanol solution of the diazoketone is irradiated under nitrogen for about one hour with a high pressure mercury lamp using a Quarz filter. The methyl 5-chloromethyl-2-thienylacetate is obtained upon work up and column chromatography on silica gel. The acetate is hydrolyzed by treatment of a 1:1 mixture of acetic acid and concentrated hydrochloric acid at room temperature overnight to give 5-chloromethyl-2-thienylacetic acid.

When in the procedure of Example 1 (B) 5-chloromethyl-2-thienylacetic acid, is substituted for p-chloromethylphenyl acetic acid, 5-chloromethyl-2-thienylacetyl chloride is obtained.

EXAMPLE 5 o-Hydroxymethylphenylacetic acid lactone

The neutral by-product obtained in Example 1 is purified by sublimation under vacuum (0.05 mm Hg at 80° C) to give o-hydroxymethylphenylacetic acid lactone. M.P. 82° C.

EXAMPLE 6 o-Bromomethylphenylacetyl chloride

To a solution of 5 ml of glacial acetic acid saturated with hydrogen bromide gas is added at 0° C a solution of o-hydroxymethylphenylacetic acid lactone (0.55 g) in 2 ml of glacial acetic acid. The mixture is stirred at room temperature for 2 hours then refluxed for 1 hour during which time hydrogen bromide gas is bubbled into the mixture. The excess lactone and solvent are removed under high vacuum at room temperature. The resulting oily residue is triturated three times with hexane to give o-bromomethylphenylacetic acid. M.P. 110° C.

A solution of 0.18 g. of o-bromomethylphenylacetic acid in excess thionyl chloride is stirred at room temperature for 18 hours after which the unreacted thionyl chloride is removed under high vacuum to give o-bromomethylphenylacetyl chloride as an oily residue.

EXAMPLE 7 o-Chloromethyl-p-methoxymandelic acid chloride

A solution of 1.1 g of 2-chloromethyl-4-methoxymandelic acid, obtained by the procedure described by B. Reichert et al., Pharmazie 5, 10 (1950), in 25 ml of thionyl chloride is stirred at room temperature for about 16 hours after which the excess thionyl chloride is removed under high vacuum to give o-chloromethyl-p-methoxymandelic acid chloride as an oil.

EXAMPLE 8

3-[(Acetyloxy)methyl]-7-amino-8-oxo-5-thia-1-azabicyclo[4.2.0.]oct-2-ene-2-carboxylic acid propionyloxymethyl ester To 35 ml of dimethyl formamide is added 7.5 g of the sodium salt of 3-[(acetyloxy)methyl]-7-amino-8-oxo-5-thia-1-azabicyclo[4.2.0]oct-2-ene-2-carboxylic acid, and the solution is stirred at room temperature for about 30 minutes after which 8 ml of chloromethylpropionate is added. Stirring is continued at room temperature for about 3 hours. The mixture is diluted with ethyl acetate and washed with water. The organic layer is separated and evaporated to dryness. The residue is recrystallized from ethyl acetate to give 3-[(acetyloxy)methyl]-7-amino-8-oxo-5-thia-1-azabicyclo[4.2.0]oct-2-ene-2-carboxylic acid propionyloxymethyl ester.

In a similar manner when an appropriate amount of chloromethylpivalate, chloromethylacetate or chloromethylbutyrate is substituted for chloromethylpropionate, the following respective products are obtained: 3-[(acetyloxy)methyl]-7-amino-8-oxo-5-thia-1-azabicyclo[4.2.0]oct-2ene-2-carboxylic acid pivalyloxymethyl ester, 3-[(acetyloxy)methyl]-7-amino-8-oxo-5-thia-1-azabicyclo[4.2.0]oct-2-ene-2-carboxylic acid acetyloxymethyl ester, 3-[(acetyloxy)methyl]-7-amino-8-oxo-5-thia-1-azabicyclo[4.2.0]oct-2-ene-2-carboxylic acid butyryloxymethyl ester.

EXAMPLE 9

3-[(Acetyloxy)methyl]-7-amino-8-oxo-5-thia-1-azabicyclo[4.2.0]oct-2-ene-2-carboxylic acid 2-amino-3-methylbutyryloxymethyl ester A suspension of 5 grams of 3-[(acetyloxy)methyl]-7-amino-8-oxo-5-thia-1-azabicyclo[4.2.0]oct-2-ene-2-carboxylic acid sodium salt and 8.5 grams of N-tert-butoxycarbonyl-L-valine chloromethyl ester, which is prepared by the general procedure described in W. German Offen. No. 2,236,620, are mixed in 100 ml of dimethyl formamide and stirred for 72 hours. The mixture is diluted with ethyl acetate, washed with water with aqueous bicarbonate and again with water. The organic layer is dried over magnesium sulfate, filtered, and evaporated to dryness to give 3-[(acetyloxy)-methyl]-7-amino-8-oxo-5-thia-1-azabicyclo[4.2.0]oct-2-ene-2carboxylic acid N-tert-butoxycarbonyl-2-amino-3-methylbutyryloxymethyl ester from which the amine protecting group is removed by standard procedures to give the title product.

EXAMPLE 10

3-[(Acetyloxy)methyl]-7-amino-8-oxo-5-thia-1-azabicyclo[4.2.0]oct-2-ene-2-carboxylic acid N-ethoxycarbonyl-N-methylaminomethyl ester 725 mg (2.5 mM) of the sodium salt of 3-[(acetyloxy)methyl]-7-amino-8-oxo-5-thia-1-azabicyclo[4.2.0]oct-2-ene-2-carboxylic acid in 50 of dimethyl formamide is treated at room temperature with 375 mg (2.5 mM) of N-chloromethyl-N-methylurethane for one hour. The mixture is carefully poured into ice water and the precipitated solid is removed by filtration and washed with water. The solid is dissolved in ethylacetate and washed with aqueous sodium bicarbonate and then with water. The organic layer is dried over magnesium sulfate filtered and evaporated to dryness in vacuo to give 3-[(acetyloxy)methyl]-7-amino-8oxo-5-thia-1-azabicyclo[4.2.0]oct-2-ene-2-carboxylic acid N-ethoxycarbonyl-N-methylaminomethyl ester.

When in the above procedure an appropriate amount of N-methyl-N-propionylaminomethyl chloride, N-butyrylaminomethyl chloride, N-acetylaminomethyl chloride, or N-methyl-N-ethoxycarbonylaminomethyl chloride is substituted for N-chloromethyl-N-methylurethane the following respective compounds are obtained:
3-[(acetyloxy)methyl]-7-amino-8-oxo-5-thia-1-azabicyclo[4.2.0]oct-2-ene-2carboxylic acid N-methyl-N-propionylaminomethyl ester,
3-[(acetyloxy)methyl]-7-amino-8-oxo-5-thia-1-azabicyclo[4.2.0]oct-2-ene2-carboxylic acid N-butyrylaminomethyl ester,
3-[(acetyloxy)methyl]-7-amino-8-oxo-5-thia-1-azabicyclo[4.2.0]oct-2ene-2-carboxylic acid N-acetylaminomethyl ester and,
3-[(acetyloxy)methyl]-7-amino-8-oxo-5-thia-1-azabicyclo[4.2.0]oct-2ene-2-carboxylic acid N-methyl-N-ethoxycarbonylaminomethyl ester.

EXAMPLE 11

3-[(Acetyloxy)methyl]-7-amino-8-oxo-5-thia-1-azabicyclo[4.2.0]oct-2-ene-2-carboxylic acid p-pivalyloxybenzyl ester To a suspension of 6.6 mM of 3-[(acetyloxy)methyl]-7-amino-8-oxo-5-thia-1-azabicyclo[4.2.0]oct-2-ene-2-carboxylic acid sodium salt in 35 ml of dimethyl formamide (DMF) is added 2 equivalents of p-pivalyloxybenzyl alcohol followed by cooling to 0° C after which 7.2 mM of dicyclohexylcarbodiimide in 7.5 ml of DMF is added dropwise with stirring. The mixture is stirred at 0° C for one hour and an additional four hours at room temperature. The formed dicyclohexylurea is removed by filtration. The filtrate is diluted with chloroform, washed with water, dried over magnesium sulfate, filtered, and evaporated in vacuo to give 3-[(acetyloxy)methyl]-7-amino-8-oxo-5-thia-1-azabicyclo[4.2.0]oct-2-ene-2-carboxylic acid p-pivalyloxybenzyl ester.

When in the above procedure an appropirate appropriate of p-(propionyloxy)benzyl alcohol, p-(acetyloxy)benzyl alcohol, or p-(valeryloxy)benzyl alcohol is substituted for p-pivalyloxybenzyl alcohol the following respective products are obtained:
3-[(acetyloxy)methyl]-7-amino-8-oxo-5-thia-1-azabicyclo[4.2.0]oct-2-ene-2-carboxylic acid p-(propionyloxy)benzyl ester,
3-[(acetyloxy)methyl]-7-amino-8-oxo-5-thia-1-azabicyclo[4.2.0]oct-2-ene-2-carboxylic acid p-(acetyloxy)benzyl ester, and
3-[(acetyloxy)methyl]-7-amino-8-oxo-5-thia-1-azabicyclo[4.2.0]oct-2ene-2-carboxylic acid p-(valeryloxy)benzyl ester.

EXAMPLE 12

3-[(2Methyl-1,3,4-thiadiazol-5-ylthio)methyl]-7-amino-8-oxo-5-thia-1azabicyclo[4.2.0]oct-2ene-2-carboxylic acid In about 1 liter of water is dissolved 0.1 mole of the sodium salt of 3-[(acetyloxy)methyl]-7-amino-8-oxo-5thia-1-azabicyclo[4.2.0]oct-2-ene-2-carboxylic acid at 70° C under nitrogen atmosphere. To the solution is added 1 equivalent of sodium bicarbonate and 2 equivalents of 2-methyl-1,3,4thiadiazol-5-ylthiol. The mixture is stirred at 70° C for 3 hours after which the pH is adjusted to 3.5, and the resulting precipitate collected giving 3-[(2-methyl-1,3,4-thiadiazol-5-ylthio)methyl]-7-amino-8-oxo-5-thia-1-azabicyclo[4.2.0]oct-2ene-2-carboxylic acid.

When in the above procedure an equivalent amount of 1,3,4-thiadiazol-5-ylthiol, 3-methyl-1,2,4-thiadiazol-5-ylthiol, tetrazol-5-ylthiol, 1-methyltetrazol-5-ylthiol or 2-methyl-1,3,4oxadiazol-5-ylthiol is substituted for 2-methyl-1,3,4-thiadiazol-5-ylthiol the following respective products are obtained:
3-[(1,3,4-thiadiazol-5-ylthio)methyl]-7-amino-8-oxo-5-thia-1-azabicyclo[4.2.0.]oct-2-ene-2-carboxylic acid,
3-[(3-methyl-1,2,4-thiadiazol-5-ylthio)methyl]-7-amino-8-oxo-5-thia-1-azabicyclo[4.2.0]oct-2-ene-2-carboxylic acid,
3-[(tetrazol-5-ylthio)methyl]-7-amino-8-oxo-5-thia-1-azabicyclo-[4.2.0]oct-2-ene-2-carboxylic acid,
3-[(1-methyltetrazol-5-ylthio)methyl]-7-amino-8-oxo-5-thia-1-azabicyclo[4.2.0]oct-2-ene-2-carboxylic acid, and
3-[(2-methyl-1,3,4oxadiazol-5-ylthio)methyl]-7-amino-8-oxo-5-thia-1-azabicyclo[4.2.0]oct-2-ene-2-carboxylic acid.

EXAMPLE 13

When in the procedure of Example 12 appropriate amounts of the sodium salt of the cephalosporin derivative and the heterocyclicthiol derivative listed below in Table IV are substituted respectively for the sodium salt of 3-[(acetyloxy)methyl]-7-amino-8-oxo-5-thia-1-azabicyclo[4.2.0]oct-2-ene-2-carboxylic acid and 2-methyl-1,3,4-thiadiazol-5-ylthio the respective products listed in Table IV are obtained.

TABLE IV

| Cephalosporin Derivative | Heterocyclicthiol | Product |
| --- | --- | --- |
| 3-[(acetyloxy)methyl]-7-amino-8-oxo-5-thia-1-azabicyclo[4.2.o]oct-2-ene-2-carboxylic acid propionyloxymethyl ester | 3-methyl-1,2,4-thiadiazol-5-ylthiol | 3-[(3-methyl-1,2,4-thiadiazol-5-ylthio)methyl]-7-amino-8-oxo-5-thia-1-azabicyclo[4.2.0]oct-2-ene-2-carboxylic acid propionyloxymethyl ester |
| 3-[(acetyloxy)methyl]-7-amino-8-oxo-5-thia-1-azabicyclo[4.2.0]oct-2-ene-2-carboxylic acid p-pivalyloxymethyl ester | 1-methyltetrazol-5-ylthiol | 3-[(1-methyltetrazol-5-ylthio)methyl]-7-amino-8-oxo-5-thia-1-azabicyclo-[4.2.0]oct-2-ene-2-carboxylic acid pivalyloxymethyl ester |
| 3-[(acetyloxy)methyl]-7-amino-8-oxo-5-thia-1-azabicyclo[4.2.0]oct-2-ene-2-carboxylic acid acetyloxymethyl ester | 1,3,4-thiadiazol-5-ylthiol | 3-[(1,3,4-thiadiazol-5-ylthio)methyl]-7-amino-8-oxo-5-thia-1-azabicyclo-[4.2.0]oct-2-ene-2-carboxylic acid acetyloxymethyl ester |
| 3-[(acetyloxy)methyl]-7-amino-8-oxo-5-thia-1-azabicyclo[4.2.0]oct-2-ene-2-carboxylic acid butyryloxymethyl ester | tetrazol-5-ylthiol | 3-[(tetrazol-5-ylthio)methyl]-7-amino-8-oxo-5-thia-1-azabicyclo[4.2.0]oct-2-ene-2-carboxylic acid butyryloxymethyl ester |
| 3-[(acetyloxy)methyl]-7-amino-8-oxo-5-thia-1-azabicyclo[4.2.0]oct-2-ene-2-carboxylic acid 2-amino-3-methylbutyryloxymethyl ester | 2-methyl-1,3,4-oxadiazol-5-ylthiol | 3-[(2-methyl-1,3,4-oxadiazol-5-yl-thio)methyl]-7-amino-8-oxo-5-thia-1-azabicyclo[4.2.0]oct-2-ene-2-carboxylic acid 2-amino-3-methylbutyryloxymethyl ester |
| 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester | 2-methyl-1,3,4-thiadiazol-5-ylthiol | 3-[(2-methyl-1,3,4-thiadiazol-5-yl-thio)methyl]-7-amino-8-oxo-5-thia-1-azabicyclo[4.2.0] oct-2-ene-2-carboxylic acid N-ethoxycarbonyl-N-methylaminomethyl ester |
| 3-[(acetyloxy)methyl]-7-amino-8-oxo-5-thia-1-azabicylo[4.2.0]oct-2-ene-2-carboxylic acid p-pivalyloxybenzyl ester | 1-methyltetrazol-5-ylthiol | 3-[(1-methyltetrazol-5-ylthio)methyl]-7-amino-8-oxo-5-thia-1-azabicyclo-[4.2.0]oct-2-ene-2-carboxylic acid p-pivalyloxybenzyl ester |
| 3-[(acetyloxy)methyl]-7-amino-7-methoxy-8-oxo-5-thia-1-azabicyclo-[4.2.0]oct-2-ene-2-carboxylic acid (prepared by acid hydrolysis of the corresponding benzhydryl ester described in U.S. patent 3,778,432) | 2-methyl-1,3,4-thiadiazol-5-ylthiol | 3-[(2-methyl-1,3,4-thiadiazol-5-yl-thio)methyl]-7-amino-7-methoxy-8-oxo-5-thia-1-azabicyclo[4.2.0]oct-2-ene-2-carboxylic acid |
| 3-[(acetyloxy)methyl]-7-amino-8-oxo-5-thia-1-azabicyclo[4.2.0]oct-2-ene-2-carboxylic acid p-(propionyloxy)benzyl ester | 1-methyltetrazol-5-ylthiol | 3-[(1-methyltetrazol-5-ylthio)methyl-7-amino-8-oxo-5-thia-1-azabicyclo-[4.2.0]oct-2-ene-2-carboxylic acid p-(propionyloxy)benzyl ester |
| 3-[(acetyloxy)methyl]-7-amino-8-oxo-5-thia-1-azabicyclo[4.2.0]oct-2-ene-2-carboxylic acid p-(acetyloxy)benzyl ester | tetrazol-5-ylthiol | 3-[(tetrazol-5-ylthio)methyl-7-amino-8-oxo-5-thia-1-azabicyclo[4.2.0]oct-2-ene-2-carboxylic acid p-(acetyloxy)-benzyl ester |

TABLE IV-continued

| Cephalosporin Derivative | Heterocyclicthiol | Product |
|---|---|---|
| 3-[(acetyloxy)methyl]-7-amino-8-oxo-5-thia-1-azabicyclo[4.2.0]oct-2-ene-2-carboxylic acid p-(valeryloxy)benzyl ester | 3-methyl-1,2,4-thiadiazol-5-ylthiol | 3-[(3-methyl-1,2,4-thiadiazol-5-ylthio)methyl]-7-amino-8-oxo-5-thia-1-azabicyclo[4.2.0]oct-2-ene-2-carboxylic acid p-(valeryloxy)benzyl ester |

EXAMPLE 14

3-[(Acetyloxy)methyl]-7-[2-[4-(chloromethyl)-phenyl]acetyl]-amino]-8-oxo-5-thia-1-azabicyclo[4.2.0-]oct-2-ene-2-carboxylic acid A mixture of 1 g of 3-[(acetyloxy)methyl]-7-amino-8-oxo-5-thia-1-azabicyclo[4.2.0]oct-2-ene-2-carboxylic acid and 1 g of p-chloromethylphenylacetyl chloride in 45 ml of ethyl acetate is refluxed for about 2 hours after which the solvent is removed under vacuum yielding a yellow-brown amorphous product which is chromatographed on silica gel using benzene-acetone as the eluant to give 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid. M.P. 164°–165° C. (dec.).

When in the procedure of Example 14 an appropriate amount of an acid chloride listed in the following Table V is substituted for p-chloromethylphenylacetyl chloride the respective cephalosporin derivatives listed in Table V are obtained. The acid chloride derivatives listed in the following Table V are obtained from the corresponding acid listed in Table I by treatment with thionyl chloride by the general procedure described in Example 1 (B).

TABLE V

| ACID CHLORIDE | CEPHALOSPORIN DERIVATIVE |
|---|---|
| p-chloromethylhydrotropic acid chloride | 3-[(acetyloxy)methyl]-7-[[2-[4-(chloromethyl)phenyl]-2-methylacetyl]amino]-8-oxo-5-thia-1-azabicyclo[4.2.0]-oct-2-ene-2-carboxylic acid |
| p-chloromethyldihydrocynnamic acid chloride | 3-[(acetyloxy)methyl]-7-[[3-[4-(chloromethyl)phenyl]propionyl]amino]-8-oxo-5-thia-1-azabicyclo[4.2.0]oct-2-ene-2-carboxylic acid |

| ACID DERIVATIVE | CEPHALOSPORIN DERIVATIVE |
|---|---|
| p-chloromethyl-2-methylhydrocynnamic acid chloride | 3-[(acetyloxy)methyl]-7-[[3-[4-(chloromethyl)phenyl]-2-methylpropionyl]amino]-8-oxo-5-thia-1-azabicyclo[4.2.0]oct-2-ene-2-carboxylic acid |
| 4-(p-chloromethylphenyl)-butyric acid chloride | 3-[(acetyloxy)methyl]-7-[[4-[4-(chloromethyl)phenyl]butyryl]amino]-8-oxo-5-thia-1-azabicyclo[4.2.0]oct-2-ene-2-carboxylic acid |
| 2-methyl-4-(p-chloromethyl-phenyl)butyric acid chloride | 3-[(acetyloxy)methyl]-7-[[4-[4-(chloromethyl)phenyl]-2-methylbutyryl]amino]-8-oxo-5-thia-1-azabicyclo[4.2.0]-oct-2-ene-2-carboxylic acid |
| p-chloromethylphenoxyacetic acid chloride | 3-[(acetyloxy)methyl]-7-[[2-[4-(chloromethyl)phenoxy]-acetyl]amino]-8-oxo-5-thia-1-azabicyclo[4.2.0]oct-2-ene-2-carboxylic acid |
| 2-(p-chloromethylphenoxy)-propionic acid chloride | 3-[(acetyloxy)methyl]-7-[[2-[4-(chloromethyl)phenoxy]-2-methylacetyl]amino]-8-oxo-5-thia-1-azabicyclo[4.2.0]oct-2-ene-2-carboxylic acid |
| 4-p-chloromethylphenoxy)butyric acid chloride | 3-[(acetyloxy)methyl]-7-[[4-[4-(chloromethyl)phenoxy]butyryl]amino]-8-oxo-5-thia-1-azabicyclo[4.2.0]oct-2-ene-2-carboxylic acid |
| 2-methyl-4-(p-chloromethyl-phenoxy)butyric acid chloride | 3-[(acetyloxy)methyl]-7-[[4-[4-(chloromethyl)phenoxy]-2-methylbutyryl]amino]-8-oxo-5-thia-1-azabicyclo[4.2.0]-oct-2-ene-2-carboxylic acid |
| 3-(p-chloromethylphenoxy)-propionic acid | 3-[(acetyloxy)methyl]-7-[[3-[4-(chloromethyl)phenoxy]-propionyl]amino]-8-oxo-5-thia-1-azabicyclo[4.2.0]oct-2-ene-2-carboxylic acid |
| p-chloromethylanilinoacetic acid chloride | 3-[(acetyloxy)methyl]-7-[[2-[4-(chloromethyl)anilino]-acetyl]amino]-8-oxo-5-thia-1-azabicyclo[4.2.0]oct-2-ene-2-carboxylic acid |
| 2-(p-chloromethyl)anilino-propionic acid chloride | 3-[(acetyloxy)methyl]-7-[[2-[4-(chloromethyl)anilino]-2-methylacetyl]amino]-8-oxo-5-thia-1-azabicyclo[4.2.0]oct-2-ene-2-carboxylic acid |
| 4-(p-chloromethylanilino)-butyric acid chloride | 3-[(acetyloxy)methyl]-7-[[4-[4-(chloromethyl)anilino]-butyryl]amino]-8-oxo-5-thia-1-azabicyclo[4.2.0]oct-2-ene-2-carboxylic acid |
| 3-(p-chloromethylanilino)-butyric acid chloride | 3-[(acetyloxy)methyl]-7-[[3-[4-(chloromethyl)anilino]-2-methylpropionyl]amino]-8-oxo-5-thia-1-azabicyclo[4.2.0]-oct-2-ene-2-carboxylic acid |
| p-chloromethylphenylthio-acetic acid chloride | 3-[(acetyloxy)methyl]-7-[[2-[4-(chloromethyl)phenylthio]-acetyl]amino]-8-oxo-5-thia-1-azabicyclo[4.2.0]oct-2-ene-2-carboxylic acid |
| 2-(p-chloromethylphenyl)-thiopropionic acid chloride | 3-[(acetyloxy)methyl]-7-[[2-[4-(chloromethyl)phenylthio]-2-methylacetyl]amino]-8-oxo-5-thia-1-azabicyclo[4.2.0]-oct-2-ene-2-carboxylic acid |
| 4-(p-chloromethylphenyl)-thiobutyric acid chloride | 3-[(acetyloxy)methyl]-7-[[4-[4-(chloromethyl)phenylthio]-butyryl]amino]-8-oxo-5-thia-1-azabicyclo[4.2.0]oct-2-ene-2-carboxylic acid |
| o-chloro-p-chloromethyl-phenylacetic acid chloride | 3-[(acetyloxy)methyl]-7-[[2-[2-(chloro)-4-(chloromethyl)-phenyl]acetyl]amino]-8-oxo-5-thia-1-azabicyclo[4.2.0]-oct-2-ene-2-carboxylic acid |
| 5-chloromethyl-2-thienylacetyl chloride | 3-[(acetyloxy)methyl]-7-[[2-[5-(chloromethyl)-2-thienyl]-acetyl]amino]-8-oxo-5-thia-1-azabicyclo[4.2.0]oct-2-ene-2-carboxylic acid |
| 2-chloromethyl-4-methoxymandelic acid chloride | 3-[(acetyloxy)methyl]-7-[[2-[2-(chloromethyl)-4-methoxy-phenyl]-2-hydroxyacetyl]-amino]-8-oxo-5-thia-1-azabicyclo[4.2.0]oct-2-ene-2-carboxylic acid |
| p-chloromethylmandelic acid chloride | 3-[(acetyloxy)methyl]-7-[[2-[4-(chloromethyl)phenyl]-2-hydroxyacetyl]amino]-8-oxo-5-thia-1-azabicyclo[4.2.0]-oct-2-ene-2-carboxylic acid |
| 3-(p-chloromethylphenyl)-lactic acid chloride | 3-[(acetyloxy)methyl]-7-[[3-[4-(chloromethyl)phenyl]-2-hydroxypropionyl]amino]-8-oxo-5-thia-1-azabicyclo[4.2.0]-oct-2-ene-2-carboxylic acid |
| 2-hydroxy-4-(p-chloro-methylphenyl)butyric acid chloride | 3-[(acetyloxy)methyl]-7-[[4-[4-(chloromethyl)phenyl]-2-hydroxybutyryl]amino]-8-oxo-5-thia-1-azabicyclo[4.2.0]-oct-2-ene-2-carboxylic acid |
| 3-(p-chloromethylphenoxy)-lactic acid chloride | 3-[(acetyloxy)methyl]-7-[[3-[4-(chloromethyl)phenoxy]-2-hydroxypropionyl]amino]-8-oxo-5-thia-1-azabicyclo-[4.2.0]oct-2-ene-2-carboxylic acid |
| 2-hydroxy-2-[2-(5-chloro-methyl)thienyl]acetic acid | 3-[(acetyloxy)methyl]-7-[[2-[5-(chloromethyl)-2-thienyl]- |

TABLE V-continued

| | |
|---|---|
| chloride | 2-hydroxyacetyl]amino]-8-oxo-5-thia-1-azabicyclo[4.2.0]-oct-2-ene-2-carboxylic acid |

EXAMPLE 15

7-[[2-[4-(Chloromethyl)phenyl]acetyl]amino]-3-methyl-8-oxo-5-thia-1-azabicyclo[4.2.0]oct-2-ene-2-carboxylic acid By the procedure of Example 14, only substituted 1 g of 7-amino-3-methyl-8-oxo-5-thia-1-azabicyclo[4.2.0-]oct-2-ene-2-carboxylic acid for 3-acetyloxymethyl-7-amino-8-oxo-5-thia-1-azabicyclo[4.2.0]oct-2-ene-2carboxylic acid, 7-[[2-[4-(chloromethyl)phenyl]acetyl]-amino]-3-methyl-8-oxo-5-thia-1-azabicyclo[4.2.0]oct-2-ene-2-carboxylic acid is obtained. M.P. 145°–146° C.

EXAMPLE 16

3-[(Acetyloxy)methyl]-7-[[2-[4-(chloromethyl)-phenyl]-2-amino-acetyl]amino]-8-oxo-5-thia-1-azabicyclo[4.2.0]oct-2-ene-2-carboxylic acid p-Chloromethylphenylglycine wherein the amino group is protected with tert-butoxycarbonyl, is treated with isobutyl chloroformate in the presence of triethylamine. The thus obtained mixed anhydride is reacted with the triethylamine salt of 3-[(acetyloxy)methyl]-7-amino-8-oxo-5-thia-1-azabicyclo[4.2.0]oct-2-ene-2carboxylic acid at 0° C for about 4 hours. The resulting product is isolated and the amine protecting group is removed by acid hydrolysis to give 3-[(acetyloxy)methyl]-7-[[2-[4-(chloromethyl)phenyl]-2-aminoacetyl]-amino]-8-oxo-5-thia-1-azabicyclo[4.2.0]oct-2-ene-2carboxylic acid.

When an appropriate amount of an amino acid listed in the following Table VI is substituted for p-chloromethylphenylglycine in the above Example 16, the corresponding cephalosporin derivative listed in the following Table VI is obtained.

TABLE VI

| AMINO ACID | CEPHALOSPORIN DERIVATIVE |
|---|---|
| 3-(p-chloromethylphenyl)-alanine | 3-[(acetyloxy)methyl]-7-[[3-[4-(chloromethyl)phenyl]-2-aminopropionyl]amino]-8-oxo-5-thia-1-azabicyclo[4.2.0]-oct-2-ene-2-carboxylic acid |
| 2-amino-4-(p-chloromethylphenyl)butyric acid | 3-[(acetyloxy)methyl]-7-[[4-[4-(chloromethyl)phenyl]-2-aminobutyryl]amino]-8-oxo-5-thia-1-azabicyclo[4.2.0]oct-2-ene-2-carboxylic acid |
| 2-amino-4-(p-chloromethylphenoxy)butyric acid | 3-[(acetyloxy)methyl]-7-[[4-[4-(chloromethyl)phenoxy]-2-aminobutyryl]amino]-8-oxo-5-thia-1-azabicyclo[4.2.0]-oct-2-ene-2-carboxylic acid |
| 3-(p-chloromethylphenoxy)-alanine | 3-[(acetyloxy)methyl]-7-[[3-[4-(chloromethyl)phenoxy]-2-aminopropionyl]amino]-8-oxo-5-thia-1-azabicyclo[4.2.0]-oct-2-ene-2-carboxylic acid |
| 2-amino-4-(p-chloromethylanilino)butyric acid | 3-[(acetyloxy)methyl]-7-[[4-[4-(chloromethyl)anilino]-2-aminobutyryl]-8-amino-5-thia-1-azabicyclo[4.2.0]oct-2-ene-2-carboxylic acid |
| 2-amino-4-(p-chloromethylphenyl)thiobutyric acid | 3-[(acetyloxy)methyl]-7-[[4-[4-(chloromethyl)phenylthio]-2-aminobutyryl]amino]-8-oxo-5-thia-1-azabicyclo[4.2.0]-oct-2-ene-2-carboxylic acid |
| 3-(p-chloromethylphenyl)-thioalanine | 3-[(acetyloxy)methyl]-7-[[3-[4-(chloromethyl)phenylthio]-2-aminopropionyl]amino]-8-oxo-5-thia-1-azabicyclo[4.2.0]-oct-2-ene-2-carboxylic acid |

TABLE VI-continued

| AMINO ACID | CEPHALOSPORIN DERIVATIVE |
|---|---|
| 2-[2-(5-chloromethyl)thienyl]glycine | 3-[(acetyloxy)methyl]-7-[[2-[5-(chloromethyl)-2-thienyl]-2-aminoacetyl]amino]-8-oxo-5-thia-1-azabicyclo[4.2.0]-oct-2-ene-2-carboxylic acid |
| 2-amino-3-[2-5-chloromethyl)thienyl]propionic acid | 3-[(acetyloxy)methyl]-7-[[3-[5-(chloromethyl)-2-thienyl] -2-aminopropionyl]amino]-8-oxo-5-thia-1-azabicyclo-[4.2.0]oct-2-ene-2-carboxylic acid |
| 2-amino-4-[2-(5-chloromethyl)thienyl]butyric acid | 3-[(acetyloxy)methyl]-7-[[4-[5-(chloromethyl)-2-thienyl]-2-aminobutyryl]amino]-8-oxo-5-thia-1-azabicyclo[4.2.0]-oct-2-ene-2-carboxylic acid |

EXAMPLE 17

3-[(Acetyloxy)methyl]-7-[[2-[4-(chloromethyl)-phenyl]-2-carboxyacetyl]amino]-8-oxo-5-thia-1-azabicyclo[4.2.0]oct-2-ene-2-carboxylic acid α-Carboxy-p-chloromethylphenylacetyl nitrophenyl polymer, prepared according to the procedure described in Canadian Pat. No. 892,580, carrying 4 m. mole of α-chloromethylphenylmalonic acid is stirred for about 8 hours in 20 ml of dry methylene chloride solution containing 1 m. mole of 3-[(acetyloxy)methyl]-7-amino-8-oxo-5-thia-1-azabicyclo[4.2.0]oct-2-ene-2-carboxylic acid triethylammonium salt, which is prepared from 544 mg of 7-aminocephalosporanic acid (1 m. mole) and 0.56 ml of triethylamine (1 m. mole) at room temperature. After only traces of 7-aminocephalosporanic acid remain in solution, which is determined by thin layer chromatography on cellulose in 70% aqueous propanol, the polymer is filtered off and washed with 3 portions of 50 ml each of methylene chloride. The combined filtrates are evaporated and the residue is dissolved in 20 ml of distilled water. This solution is acidified to pH 2 by adding 0.2N hydrochloric acid and extracted twice with ethyl acetate. The organic solution is dried over sodium sulfate and evaporated at room temperature. The reamaining solid is dried over night over phosphorus pentoxide under vacuum to give 3-[(acetyloxy)methyl]-7-[[2-[4-(chloromethyl)phenyl]-2-carboxyacetyl]amino]-8-oxo-5-thia-1-azabicyclo[4.2.0]oct-2-ene-2-carboxylic acid.

When in the procedure of Example 17 an appropriate amount of an acid listed in the following Table VII is substituted for p-chloromethylphenylmalonic acid the respective cephalosporin derivative listed in Table VII are obtained

TABLE VII

| ACID | CEPHALOSPORIN DERIVATIVE |
|---|---|
| 2-sulfo-p-chloromethylphenylacetic acid | 3-[(acetyloxy)methyl]-7-[[2-[4-(chloromethyl)phenyl]-2-sulfoacetyl]amino]-8-oxo-5-thia-1-azabicylco[4.2.0]oct-2-ene-1-carboxylic acid |
| 4-(p-chloromethylphenyl)-2-sulfobutyric acid | 3-[(acetyloxy)methyl]-7-[[4-[4-(chloromethyl)phenyl]-2-sulfobutyryl]amino]-8-oxo-5-thia-1-azabicyclo[4.2.0]oct-2-ene-2-carboxylic acid |
| p-chloromethylbenzylmalonic acid | 3-[acetyloxy)methyl]-7-[[3-[4-chloromethyl)phenyl]-2-carboxypropionyl]amino]-8-oxo-5-thia-1-azabicylco[4.2.0]-oct-2-ene-2-carboxylic acid |
| 2-(p-cloromethylphenoxy)-ethylmalonic acid | 3-[(acetyloxy)methyl]-7-[[4-(chloromethyl)phenoxy]-2-carboxybutyryl]amino]-8-oxo- |

TABLE VII-continued

| ACID | CEPHALOSPORIN DERIVATIVE |
|---|---|
| | 5-thia-1-azabicyclo[4.2.0]-oct-2-ene-2-carboxylic acid |
| 2-(p-chloromethylphenyl-thioethylmalonic acid | 3-[(acetyloxy)methyl]-7-[[4-[4-(chloromethyl)phenylthio]-2-carboxybutyryl]amino]-8-oxo-5-thia-1-azabicyclo[4.2.0]oct-2-ene-2-carboxylic acid |
| p-chloromethylanilinomethyl-malonic acid | 3-[(acetyloxy)methyl]-7-[[3-[4-(chloromethyl)anilino]-2-carboxypropionyl]amino]-8-oxo-5-thia-1-azabicyclo[4.2.0]-oct-2-ene-2-carboxylic acid |
| 2-[2-(5-chloromethyl)-thienyl]malonic acid | 3-[(acetyloxy)methyl]-7-[[3-[5-(chloromethyl)-2-thienyl]-2-carboxypropionyl]amino]-8-oxo-5-thia-1-azabicyclo[4.2.0]oct-2-ene-2-carboxylic acid |

EXAMPLE 18

3-[(acetyloxy)methyl]-7-[[2-[4-(chloromethyl)-phenyl]acetyl]-amino]-8-oxo-5-thia-1-azabicyclo[4.2.0-]oct-2-ene-2-carboxylic acid pivalyloxy methyl ester A mixture of 1 g of 3-[(acetyloxy)methyl]-7-amino-8-oxo-5-thia-1-azabicyclo[4.2.0]oct-2-ene-2-carboxylic acid pivalyloxy methyl ester and 1 g of p-chloromethyl-phenyl acetyl chloride in 45 ml of ethyl acetate is refluxed for about 2 hours after which the solvent is removed under vacuum yielding a product which is chromatographed on silica gel using benzene-acetone as the eluant to give 3-[(acetyloxy)methyl]-7-[[2-[4-(chloromethyl)-phenyl]acetyl]amino]-8-oxo-5-thia-1-azabicyclo[4.2.0]oct-2-ene-2-carboxylic aid pivalyloxy methyl ester.

When in the procedure of Example 18 an appropriate amount of a 7-aminocephalosporanic acid derivative listed in the following Table VIII is substituted for 3-[(acetyloxy)methyl]-7-amino-8-oxo-5-thia-1-azabicyclo[4.2.0]oct-2-ene-2-carboxylic acid pivalyloxy methyl ester and an appropriate amount of the acid chloride listed in the following Table VIII is substituted for p-chloromethylphenylacetyl chloride, the respective products listed in Table VIII are obtained.

TABLE VIII

| ACID CHLORIDE | 7-AMINOCEPHALOSPORANIC ACID DERIVATIVE | PRODUCT |
|---|---|---|
| p-chloromethylhydrotropic acid chloride | 3-[(acetyloxy)methyl]-7-amino-8-oxo-5-thia-1-azabicyclo[4.2.0]-oct-2-ene-2-carboxylic acid propionyloxymethyl ester | 3-[(acetyloxy)methyl]-7-[[2-[4-(chloromethyl)-phenyl]-2-methylacetyl]-amino]-8-oxo-5-thia-1-azabicyclo[4.2.0]oct-2-ene-2-carboxylic acid propionyloxymethyl ester |
| p-chloromethyl-2-methyl-hydrocynnamic acid chloride | 3-[(acetyloxy)methyl]-7-amino-8-oxo-5-thia-1-azabicyclo[4.2.0]-oct-2-ene-2-carboxylic acid acetyloxymethyl ester | 3-[(acetyloxy)methyl]-7-[[3-[4-(chloromethyl-phenyl]-2-methylpropionyl]-amino]-8-oxo-5-thia-1-azabicyclo[4.2.0]oct-2-ene-2-carboxylic acid acetyloxymethyl ester |
| 2-methyl-4-(p-chloromethyl-phenyl)butyric acid chloride | 3-[(acetyloxy)methyl]-7-amino-8-oxo-5-thia-1-azabicyclo[4.2.0]-oct-2-ene-2-carboxylic acid butyryloxymethyl ester | 3-[(acetyloxy)methyl]-7-[[4-[4-(chloromethyl)-phenyl]-2-methylbutyryl]-amino]-8-oxo-5-thia-1-azabicyclo[4.2.0]oct-2-ene-2-carboxylic acid butyryloxymdethyl ester |
| 2-(p-chloromethylphenoxy)-propionic acid chloride | 3-[(acetyloxy)methyl]-7-amino-8-oxo-5-thia-1-azabicyclo[4.2.0]-oct-2-ene-2-carboxylic acid 2-amino-3-methylbutyryloxymethyl ester | 3-[(acetyloxy)methyl]-7-[[2-[4-(chloromethyl)-phenoxy]-2-methylacetyl]-amino]-8-oxo-5-thia-1-azabicyclo[4.2.0]oct-2-ene-2-carboxylic acid 2-amino-3-methylbutyryloxy-methyl ester |
| 2-methyl-4-(p-chloromethyl-phenoxy)butyric acid chloride | 3-[(acetyloxy)methyl]-7-amino-8-oxo-5-thia-1-azabicylo[4.2.0]-oct-2-ene-2-carboxylic acid N-ethoxycarbonyl-N-methylamino-methyl ester | 3-[(acetyloxy)methyl]-7-[[4-[4-(chloromethyl)-phenoxy]-2-methylbutyryl]-amino]-8-oxo-5-thia-1-azabicyclo[4.2.0]oct-2-ene-2-carboxylic acid N-ethoxycarbonyl-N-methyl-aminoethyl ester |
| p-chloromethylanilinoacetic acid chloride | 3-[(acetyloxy)methyl]-7-amino-8-oxo-5-thia-1-azabicyclo[4.2.0]-oct-2-ene-2-carboxylic acid N-methyl-N-propionylaminomethyl ester | 3-[(acetyloxy)methyl]-7-[[2-[4-(chloromethyl)-anilino]acetyl]amino]-8-oxo-5-thia-1-azabicyclo-[4.2.0]oct-2-ene-2-carboxylic acid N-methyl-N-propionylaminomethyl ester |
| 4-(p-chloromethylanilino)-butyric acid chloride | 3-[(acetoyloxy)methyl]-7-amino-8-oxo-5-thia-1-azabicyclo[4.2.0]-oct-2-ene-2-carboxylic acid N-butyrylaminomethyl ester | 3-[(acetyloxy)methyl]-7-[[4-[4-(chloromethyl)-anilino]butyryl]amino]-8-oxo-5-thia-1-azabicyclo[4.2.0]oct-2-ene-2-carboxylic acid N-butyryl-aminomethyl ester |
| p-chloromethylphenylthio-acetic acid chloride | 3-[(acetyloxy)methyl]-7-amino-8-oxo-5-thia-1-azabicyclo[4.2.0]-oct-2-ene-2-carboxylic acid N-acetylaminomethyl ester | 3-[(acetyloxy)methyl]-7-[[2-[4-(chloromethyl)-phenylthio]acetyl]amino]-8-oxo-5-thia-1-azabicyclo[4.2.0]oct-2-ene-2-carboxylic acid N-acetyl- |

TABLE VIII-continued

| ACID CHLORIDE | 7-AMINOCEPHALOSPORANIC ACID DERIVATIVE | PRODUCT |
| --- | --- | --- |
| 4-(p-chloromethylphenyl)-thiobutyric acid chloride | 3-[(acetyloxy)methyl]-7-amino-8-oxo-5-thia-1-azabicyclo[4.2.0]-oct-2-ene-2-carboxylic acid N-methyl-N-ethoxycarbonylaminomethyl ester | aminomethyl ester 3-[(acetyloxy)methyl]-7-[[4-[4-(chloromethyl)-phenylthio]butyryl]amino]-8-oxo-5-thia-1-azabicyclo[4.2.0]oct-2-ene-2-carboxylic acid N-methyl-N-ethoxycarbonylaminomethyl ester |
| 5-chloromethyl-2-thienyl-acetyl chloride | 3-[(acetyloxy)methyl]-7-amino-8-oxo-5-thia-1-azabicyclo[4.2.0]-oct-2-ene-2-carboxylic acid p-pivalyloxybenzyl ester | 3-[(acetyloxy)methyl]-7-[[2-[5-(chloromethyl)-2-thienyl]acetyl]amino]-8-oxo-5-thia-1-azabicyclo-[4.2.0]oct-2-ene-2-carboxylic acid p-pivalyloxy-benzyl ester |
| p-chloromethylmandelic acid chloride | 3-[(acetyloxy)methyl]-7-amino-8-oxo-5-thia-1-azabicyclo[4.2.0]-oct-2-ene-2-carboxylic acid p-(propionyloxy)benzyl ester | 3-[(acetyloxy)methyl]-7-[[2-[4-(chloromethyl)-phenyl[-2-hydroxyacetyl]-amino]-8-oxo-5-thia-1-azabicyclo[4.2.0]oct-2-ene-2-carboxylic acid p-(propionyloxy)benzyl ester |
| 2-hydroxy-4-(p-chloromethyl-phenyl)butyric acid chloride | 3-[(acetyloxy)methyl]-7-amino-8-oxo-5-thia-1-azabicyclo[4.2.0]-oct-2-ene-2-carboxylic acid p-(acetyloxy)benzyl ester | 3-[(acetyloxy)methyl]-7-[[4-[4-(chloromethyl)-phenyl]-2-hydroxybutyryl]-amino]-8-oxo-5-thia-1-azabicyclo[4.2.0]oct-2-ene-2-carboxylic acid p-(acetyloxy)benzyl ester |
| 2'-hydroxy-2'-[2-(5-chloromethyl)thienyl]-acetic acid chloride | 3-[(acetyloxy)methyl]-7-amino-8-oxo-5-thia-1-azabicyclo[4.2.0]-oct-2-ene-2-carboxylic acid p-(valyryloxy)benzyl ester | 3-[(acetyloxy)methyl]-7-[[2-[5-(chloromethyl)-2-thienyl]-2-hydroxyacetyl]-amino]-8-oxo-5-thia-1-azabicyclo[4.2.0]oct-2-ene-2-carboxylic acid p-(valyryloxy)benzyl ester |
| p-chloromethylphenyl-acetyl chloride | 3-[(2-methyl-1,3,4-thiadiazol-5-ylthio)methyl]-7-amino-8-oxo-5-thia-1-azabicyclo[4.2.0]oct-2-ene-2-carboxylic acid | 3-[(2-methyl-1,3,4-thiadiazol-5-ylthio)methyl]-7-[[2-[4-(chloromethyl)phenyl]acetyl]amino]-8-oxo-5-thia-1-azabicyclo[4.2.0]-oct-2-ene-2-carboxylic acid |
| p-chloromethylphenoxy-acetic acid chloride | 3-[(1,3,4-thiadiazol-5-ylthio)-methyl]-7-amino-8-oxo-5-thia-1-azabicyclo[4.2.0]oct-2-ene-2-carboxylic acid | 3-[(1,3,4-thiadiazol-5-ylthio)methyl]-7-[[2-[4-(chloromethyl)phenoxy]-acetyl]amino]-8-oxo-5-thia-1-azabicyclo[4.2.0]-oct-2-ene-2-carboxylic acid |
| p-chloromethyldihydro-cynnamic acid chloride | 3-[(3-methyl-1,2,4-thiadiazol-5-ylthio)methyl]-7-amino-8-oxo-5-thia-1-azabicyclo[4.2.0]oct-2-ene-2-carboxylic acid | 3-[(3-methyl-1,2,4-thiadiazol-5-ylthio)methyl]-7-[[3-[4-(chloromethyl)phenyl]-propionyl]amino]-8-oxo-5-thia-1-azabicyclo[4.2.0]-oct-2-ene-2-carboxylic acid |
| 4-(p-chloromethylphenyl)-butyric acid chloride | 3-[(tetrazol-5-ylthio)methyl]-7-amino-8-oxo-5-thia-1-azabicyclo-[4.2.0]oct-2-ene-2-carboxylic acid | 3-[(tetrazol-5-ylthio)-methyl]-7-[[4-[4-(chloro-methyl)phenyl]butyryl]-amino]-8-oxo-5-thia-1-aza bicyclo[4.2.0]oct-2-ene-2-carboxylic acid |
| p-chloromethylphenylacetyl chloride | 3-[(1-methyltetrazol-5-ylthio)-methyl]-7-amino-8-oxo-5-thia-1-azabicyclo[4.2.0]oct-2-ene-2-carboxylic acid | 3-[(1-methyltetrazol-5-yl-thio)methyl]-7-[[2-[4-(chloromethyl)phenyl]ace-tyl]amino]-8-oxo-5-thia-1-azabicyclo[4.2.0]oct-2-ene-2-carboxylic acid |
| 4-(p-chloromethylphenoxy)-butyric acid chloride | 3-[(2-methyl-1,3,4-oxadiazol-5-ylthio)methyl]-7-amino-8-oxo-5-thia-1-azabicyclo[4.2.0]oct-2-ene-2-carboxylic acid | 3-[(2-methyl-1,3,4-oxadia-zol-5-ylthio)methyl]-7-[[4-[4-(chloromethyl)phenyl]-butyryl]amino]-8-oxo-5-thia-1-azabicyclo[4.2.0]oct-2-ene-2-carboxylic acid |
| 3-(p-chloromethylphenoxy)-propionic acid | 3-[(3-methyl-1,2,4-thiadiazol-5-ylthio)methyl]-7-amino-8-oxo-5-thia-1-azabicyclo[4.2.0]oct-2-ene-2-carboxylic acid propionyl-oxymethyl ester | 3-[(3-methyl-1,2,4-thiadia-zol-5-ylthio)methyl]-7-[[3-[4-(chloromethyl)phenoxy]-propionyl]amino]-8-oxo-5-thia-1-azabicyclo[4.2.0]-oct-2-ene-2-carboxylic acid propionyloxymethyl ester |
| 2-(p-chloromethyl)anilino-propionic acid chloride | 3-[(1-methyltetrazol-5-ylthio)-methyl]-7-amino-8-oxo-5-thia-1-azabicyclo[4.2.0]oct-2-ene-2-carboxylic acid pivalyloxymethyl ester | 3-[(1-methyltetrazol-5-yl-thio)methyl]-7-[[2-[4-(chloromethyl)anilino]-2-methylacetyl]amino]-8-oxo-5-thia-1-azabicyclo[4.2.0]-oct-2-ene-2-carboxylic acid pivalyloxymethyl ester |

TABLE VIII-continued

| ACID CHLORIDE | 7-AMINOCEPHALOSPORANIC ACID DERIVATIVE | PRODUCT |
|---|---|---|
| 3-(p-chloromethylanilino)-butyric acid chloride | 3-[(1,3,4-thiadiazol-5-ylthio)-methyl]-7-amino-8-oxo-5-thia-1-azabicyclo[4.2.0]oct-2-ene-2-carboxylic acid acetyloxymethyl ester | 3-[(1,3,4-thiadiazol-5-ylthio)methyl]-7-[[3-[4-(chloromethyl)anilino]-2-methylpropionyl]amino]-8-oxo-5-thia-1-azabicyclo-[4.2.0]oct-2-ene-2-carboxylic acid acetyloxymethyl ester |
| 2-(p-chloromethylphenyl)-thiopropionic acid chloride | 3-[(tetrazol-5-ylthio)methyl]-7-amino-8-oxo-5-thia-1-azabicyclo-[4.2.0]oct-2-ene-2-carboxylic acid butyryloxymethyl ester | 3-[(tetrazol-5-ylthio)methyl]-7-[[2-[4-(chloromethyl)phenylthio]-2-methylacetyl]-amino]-8-oxo-5-thia-1-azabicyclo[4.2.0]oct-2-ene-2-carboxylic acid butyryloxymethyl ester |
| o-chloro-p-chloromethyl-phenylacetic acid chloride | 3-[(2-methyl-1,3,4-oxadiazol-5-ylthio)methyl]-7-amino-8-oxo-5-thia-1-azabicyclo[4.2.0]oct-2-ene-2-carboxylic acid 2-amino-3-methylbutyryloxymethyl ester | 3-[(2-methyl-1,3,4-oxadiazol-5-ylthio)methyl]-7-[[2-[2-(chloro)-4-(chloromethyl)-phenyl]acetyl]amino]-8-oxo-5-thia-1-azabicyclo[4.2.0]-oct-2-ene-2-carboxylic acid 2-amino-3-methylbutyryloxymethyl ester |
| 2-chloromethyl-4-methoxy-mandelic acid chloride | 2-[(2-methyl-1,3,4-thiadiazol-5-ylthio)methyl]-7-amino-8-oxo-5-thia-1-azabicyclo[4.2.0]oct-2-ene-2-carboxylic acid N-ethoxycarbonyl-N-methylaminomethyl ester | 3-[(2-methyl-1,3,4-thiadiazol-5-ylthio)methyl]-7-[[2-[2-(chloromethyl)-4-methoxyphenyl]-2-hydroxyacetyl]amino]-8-oxo-5-thia-1-azabicyclo[4.2.0]oct-2-ene-2-carboxylic acid N-ethoxycarbonyl-N-methylaminomethyl ester |
| 3-(p-chloromethylphenyl)-lactic acid chloride | 3-[(1-methyltetrazol-5-ylthio)-methyl]-7-amino-8-oxo-5-thia-1-azabicyclo[4.2.0]oct-2-ene-2-carboxylic acid p-pivalyloxybenzyl ester | 3-[(1-methyltetrazol-5-ylthio)methyl]-7-[[3-[4-(chloromethyl)phenyl]-2-hydroxypropionyl]amino]-8-oxo-5-thia-1-azabicyclo-[4.2.0]oct-2-ene-2-carboxylic acid p-pivalyloxybenzyl ester |

EXAMPLE 19

7-Amino-3-methyl-[-oxo-5-thia-1azabicyclo[4.2.0-]oct-2-ene-2-carboxylic acid pivalyloxymethyl ester To 35 ml of dimethylformamide is added 7.5 g of the sodium salt of 7-amino-3-methyl-8-oxo-5-thia-1-azabicyclo[4.2.0]oct-2-ene-2-carboxylic acid and the solution is stirred at room teemperature for about 30 minutes after which 8 ml of chloromethylpivalate is added. Stirring is continued at room temperature for about 3 hours. The mixture is diluted with ethylacetate and washed with water. The organic layer is separated, evaporated to dryness, and the residue is recrystallized from ethylacetate to give 7-amino-3-methyl-8-oxo-5-thia-1-azabicyclo[4.2.0]oct-2-ene-2-carboxylic acid pivalyloxymethyl ester.

In a similar manner when an appropriate amount of chloromethylpropionate, chloromethylacetate or chloromethylbutyrate is substituted for chloromethylpivalate in the above procedure, the following respective products are obtained.
7-amino-3-methyl-8-oxo-5-thia-1-azabicyclo[4.2.0]oct-2-ene-2-carboxylic acid propionyloxymethyl ester
7-amino-3-methyl-8-oxo-5-thia-1-azabicyclo[4.2.0]oct-2-ene-2-carboxylic acid acetyloxymethyl ester 7-amino-3-methyl-8-oxo-5-thia-1-azabicyclo[4.2.0]oct-2-ene-2-carboxylic acid butyryloxymethyl ester.

When in the procedure of Example 16 an appropriate amount of 7-amino-3-methyl-8-oxo-5-thia-1-azabicyclo[4.2.0]-oct-2-ene-2-carboxylic acid or the corresponding pivalyloxymethyl ester is substituted for 3-[(acetyloxy)-methyl]-7-amino-8-oxo-5-thia-1azabicyclo[4.2.0]-oct-2-ene-2-carboxylic acid, 3-methyl-7-[[2-[4-(chloromethyl)-phenyl]-2-aminoacetyl]amino]-8-oxo-5-thia-1-azabicyclo-[4.2.0]oct-2-ene-2-carboxylic acid and 3-methyl-7-[[2-[4-(chloromethyl)phenyl]-2-aminoacetyl]amino]-8-oxo-5-thia-1-azabicyclo[4.2.0-]oct-2-ene-2-carboxylic acid pivalyloxymethyl ester are obtained.

EXAMPLE 20

3-[(2-methyl-1,3,4-thiadiazol-5-ylthio)methyl[-7-[[2-[4-(chloromethyl)phenyl[-2-aminoacetyl]amino]-8-oxo-5-thia-1-azabicyclo[4.2.0]oct-2-ene-2-carboxylic acid p-Chloromethylphenylglycine wherein the amino group is protected with tert-butoxycarbonyl is treated with isobutylchloroformate in the presence of triethylamine. The thus obtained anhydride is reacted with the triethylamine salt of 3-[(2-methyl-1,3,4-thiadiazol-5-ylthio)methyl]-7-amino-8-oxo-5-thia-1-azabicyclo[4.2.0-]oct-2-ene-2-carboxylic acid at 0° C for about 4 hours. The resulting product is isolated, and the amine protecting group is removed by acid hydrolysis and the amine protecting group is removed by acid hydrolysis to give 3-[(2-methyl-1,3,4-thiadiazol-5-ylthio)methyl]-7-[[2-[4-(chloromethyl)phenyl]-2-aminoacetyl]amino]-8-oxo-5-thia-1-azabicyclo[4.2.0]oct-2-ene-2-carboxylic acid.

When appropriate amounts of an amino acid derivative and a 7-aminocephalosporanic acid derivative listed in the following Table IX are substituted respectively for p-chloromethylphenylglycine and 3-[(2-methyl-1,3,4-thiadazol-5-ylthio)methyl]-7-amino-8-oxo-5-thia-1-azabicyclo[4.2.0]oct-2-ene-2-carboxylic acid in the above procedure, the respective products listed in the following Table IX are obtained.

TABLE IX

| AMINO ACID | 7-AMINOCEPHALOSPORANIC ACID DERIVATIVE | PRODUCT |
| --- | --- | --- |
| 3-(p-chloromethylphenyl)-alanine | 3-[(1,3,4-thiadiazol-5-ylthio)-methyl]-7-amino-8-oxo-5-thia-1-azabicyclo[4.2.0]oct-2-ene-2-carboxylic acid | 3-[(1,3,4-thiadiazol-5-ylthio)methyl]-7-[[3-[4-(chloromethyl)phenyl]-2-aminopropionyl]amino]-8-oxo-5-thia-1-azabicycylo[4.2.0]oct-2-ene-2-carboxylic acid |
| 2-amino-4-(p-chloromethyl-phenoxy)butyric acid | 3-[(3-methyl-1,2,4-oxadiazol-5-ylthio)methyl]-7-amino-8-oxo-5-thia-1-azabicyclo[4.2.0]-oct-2-ene-2-carboxylic acid | 3-[(3-methyl-1,2,4-thiadiazol-5-ylthio)methyl]-7-[[4-[4-(chloromethyl)phenoxy]-2-aminobutyryl]amino]-8-oxo-5-thia-1-azabicyclo[4.2.0]oct-2-ene-2-carboxylic acid |
| 3-(p-chloromethylphenoxy)-alanine | 3-[(tetrazol-5-ylthio)methyl]-7-amino-8-oxo-5-thia-1-azabicyclo[4.2.0]oct-2-ene-2-carboxylic acid | 3-[(tetrazol-5-ylthio)-methyl]-7-[[3-[4-(chloromethyl)phenoxy]-2-aminopropionyl]amino]-8-oxo-5-thia-1-azabicyclo[4.2.0]-oct-2-ene-2-carboxylic acid |
| 2-amino-4-(p-chloromethyl-phenyl)thiobutyric acid | 3-[(1-methyltetrazol-5-ylthio)-methyl]-7-amino-8-oxo-5-thia-1-azabicyclo[4.2.0]oct-2-ene-2-carboxylic acid | 3-[(1-methyltetrazol-5-ylthio)methyl]-7-[[4-[4-(chloromethyl)phenylthio]-2-aminobutyryl]amino]-8-oxo-5-thia-1-azabicyclo-[4.2.0]oct-2-ene-2-carboxylic acid |
| 2-[2-(5-chloromethyl)-thienyl]glycine | 3-[(2-methyl-1,3,4-oxadiazol-5-ylthio)methyl]-7-amino-8-oxo-5-thia-1-azabicyclo[4.2.0]oct-2-ene-2-carboxylic acid | 3-[(2-methyl-1,3,4-oxadiazol-5-ylthio)methyl]-7-[[2-[5-(chloromethyl)-2-thienyl]-2-aminoacetyl]-amino]-8-oxo-5-thia-1-azabicyclo[4.2.0]oct-2-ene-2-carboxylic acid |

EXAMPLE 21

3-[(Acetyloxy)methyl]-7-[[2-[4-(chloromethyl)phenyl]-2-aminoacetyl]amino]-8-oxo-5-thia-1-azabicyclo[4.2.0-]oct-2-ene-2-carboxylic acid pivalyloxymethyl ester p-Chloromethylphenylglycine wherein the amino group is protected with tert-butoxycarbonyl is treated with isobutyl chloroformate in the presence of triethylamine. The thus obtained mixed anhydride is reacted with 3[(acetyloxy)methyl]-7-amino-8-oxo-5-thia-1-azabicyclo[4.2.0]oct-2-ene-2-carboxylic acid pivalyloxymethyl ester at 0° C for about 3 hours. The resulting product is isolated, and the amine protecting group is removed by acid hydrolysis by treating the product with difluoroacetic acid for 5 minutes at room temperature to give 3-[(acetyloxy)methyl]-7[[2-[4-(chloromethyl)phenyl]-2-aminoacetyl]amino]-8oxo-5-thia-1-azabicyclo[4.2.0]oct-2-ene-2-carboxylic acid pivalyloxymethyl ester.

When in the above procedure an appropriate amount of 3-[(1-methyltetrazol-5-ylthio)methyl]-7-amino-8-oxo-5-thia-1-azabicyclo[4.2.0]oct-2-ene-2-carboxylic acid pivalyloxymethyl ester is substituted for 3-[(acetyloxy)-methyl]-7-amino-8-oxo-5-thia-1-azabicyclo[4.2.0]oct-2-ene-2-carboxylic acid pivalyloxymethyl ester, the following compound is obtained: 7-[[2-[4-(chloromethyl)phenyl]-2-aminoacetyl]-3-[(1-methyltetrazol-5-ylthio)methyl]-8-oxo-5-thia-1-azabicyclo-[4.2.0]oct-2-ene-2-carboxylic acid pivalyloxymethyl ester

EXAMPLE 22

7-[[2-[4-(Chloromethyl)phenyl]-2-carboxyacetyl]-amino]-3-[(2-methyl-1,3,4-thiadiazol-5-ylthio)methyl]-8-oxo-5-thia-1-azabicyclo[4.2.0]oct-2-ene-2-carboxylic acid α-Carboxy-p-chloromethylphenylacetylnitrophenyl polymer, prepared according to the procedure described in Canadian Pat. No. 892,580, carrying 4m. mole of p-chloromethyl phenylmalonic acid is suspended for about 8 hours in 20 ml of dry methylene chloride solution containing 1 m. mole of 3-[(2-methyl-1,3,4-thiadiazol-5-ylthio)methyl]-7-amino-8-oxo-5-thia-1-azabicyclo[4.2.0]oct-2-ene-2-carboxylic acid triethylammonium salt, which is prepared from the 7-aminocephalosporanic acid derivative and triethylamine at room temperature. After only traces of 3-[(2-methyl-1,3,4-thiadiazol-5-ylthio)methyl]-7-amino-8-oxo-5-thia-1-azabicyclo[4.2.0]oct-2-ene-2-carboxylic acid remain in solution, which is determined by thin layer chromatography on cellulose in 70% aqueous propanol, the polymer is filtered off and washed with three portions of 50 ml each of methylene chloride. The combined filtrates are evaporated and the residue is dissolved in 20 ml of distilled water. This solution is acidified to pH 2 by adding 0.2 N hydrochloric acid and extracted twice with ethylacetate. The organic solution is dried over sodium sulfate and evaporated to room temperature. The remaining solid is dried overnight over phosphorus pentoxide under vacuum to give 7-[[2-[4-chloromethyl)phenyl]-2-carboxyacetyl]amino]-3-[(2-methyl-1,3,4-thiadiazol-5-yl-thio)methyl]-8-oxo-5-thia-1-azabicyclo[4.2.0]oct-2-ene-2-carboxylic acid.

When

When in the above procedure appropriate amounts of an acid derivative and a cephalosporin derivative listed in the following Table X are substituted respectively for p-chloro-methylphenylmalonic acid and 3-(2-methyl-1,3,4-thiadiazol-5-ylthio)methyl]-7-amino-8-oxo-5-thia-1-azabicyclo]4.2.0]oct-2-ene-2-carboxylic acid in the above procedure, the respective products listed in the following Table X are obtained.

TABLE X

| ACID DERIVATIVE | CEPHALOSPORIN DERIVATIVE | PRODUCT |
|---|---|---|
| 2-sulfo-p-chloromethyl-phenylacetic acid | 3-[(1,3,4-thiadiazol-5-ylthio)-methyl]-7-amino-8-oxo-5-thia-1-azabicyclo[4.2.0]oct-2-ene-2-carboxylic acid | 7-[[2-[4-(chloromethyl)-phenyl]-2-sulfoacetyl]-amino]-3-[(1,3,4-thiadiazol-5-ylthio)methyl]-8-oxo-5-thia-1-azabicyclo[4.2.0]-oct-2-ene-2-carboxylic acid |
| 4-(p-chloromethylphenyl)-2-sulfobutyric acid | 3-[(3-methyl-1,2,4-thiadiazol-5-ylthio)methyl]-7-amino-8-oxo-5-thia-1-azabicyclo[4.2.0]oct-2-ene-2-carboxylic acid | 7-[[4-[4-(chloromethyl)phenyl]-2-sulfobutyryl]amino]-3-[(3-methyl-1,2,4-thiadiazol-5-ylthio)methyl]-8-oxo-5-thia-1-azabicyclo[4.2.0]oct-2-ene-2-carboxylic acid |
| 2-(p-chloromethylphen-oxy)ethylmalonic acid | 3-[(tetrazol-5-ylthio)methyl]-7-amino-8-oxo-5-thia-1-azabicyclo[4.2.0]oct-2-ene-2-carboxylic acid | 7-[[4-[4-(chloromethyl)phen-oxy]-2-carboxybutyryl]amino]-3-[(tetrazol-5-ylthio)methyl]-8-oxo-5-thia-1-azabicyclo-[4.2.0]oct-2-ene-2-carboxylic acid |
| p-chloromethylanilino-methylmalonic acid | 3-[(1-methyltetrazol-5-ylthio)-methyl]-7-amino-8-oxo-5-thia-1-azabicyclo[4.2.0]oct-2-ene-2-carboxylic acid | 7-[[3-[4-(chloromethyl)ani-lino]-2-carboxypropionyl]-amino]-3-[(1-methyltetrazol-5-ylthio)methyl]-8-oxo-5-thia-1-azabicyclo[4.2.0]oct-2-ene-2-carboxylic acid |
| 2-[2-(5-chloromethyl)-thenyl]malonic acid | 3-[(2-methyl-1,3,4-oxadiazol-5-ylthio)methyl]-7-amino-8-oxo-5-thia-1-azabicyclo[4.2.0]-oct-2-ene-2-carboxylic acid | 7-[[3-[5-(chloromethyl)-2-thienyl]-2-carboxypropionyl]-amino]-3-[(2-methyl-1,3,4-oxa-diazol-5-ylthio)methyl]-8-oxo-5-thia-1-azabicyclo[4.2.0]-oct-2-ene-2-carboxylic acid |

EXAMPLE 23

3[(Acetyloxy)methyl]-7-[[2-[4-(chloromethyl)-phenyl]-2-carboxyacetyl]amino[-8oxo-5-thia-1-azabicyclo[4.2.0]-oct-2-ene-2-carboxylic acid propionyloxymethyl ester α-Carboxy-p-chloromethylphenylacetylnitrophenyl polymer prepared as in the procedure of Example 22, carrying four m. mole of p-chloromethylphenylmalonic acid was suspended for about 8 hours in 20 ml of dry methylene chloride solution containing 1 millimole of 3-[(acetyloxy)methyl]-7-amino-8-oxo-5-thia-1-azabicyclo[4.2.0]oct-2-ene-2-carboxylic acid propionyloxymethyl ester. After only traces of the 7-amino-cephalosporanic acid ester derivative remain in solution, which is determined by thin layer chromatography on cellulose in 70% aqueous propanol, the polymer is filtered off and washed with portions of 50 ml each of methylene chloride. The combined filtrates are evaporated and the residue is dissolved in 20 ml of distilled water. The solution is acidified to a pH of 2 by adding 0.2 normal hydrochloric acid and extracted twice with ethylacetate. The organic solution is dried over sodium sulfate and evaporated at room temperature. The remaining solid is dried overnight over phosphorus pentoxide under vacuum to give 3-[(acetyloxy)-methyl]-7-[[2-[4-(chloromethyl)phenyl]-2-carboxyacetyl]-amino]-8-oxo-5-thia-1-azabicyclo[4.2.0]-oct-2-ene-2-carboxylic acid propionyloxymethyl ester.

When in the above procedure an appropriate amount of 7-amino-3-[(2-methyl-1,3,4-thiadiazol-5-ylthio)methyl]-8-oxo-5-thia-1-azabicyclo[4.2.0]oct-2-ene-2-carboxylic acid propionyloxymethyl ester is substituted for 3-[(acetyloxy)-methyl]-7-amino-8-oxo-5-thia-1-azabicyclo]4.2.0]oct-2-ene-2-carboxylic acid propionyloxymethyl ester the following product is obtained: 7-[[2-[4-(chloromethyl)phenyl]-2-carboxyacetyl]amino]-3-[(2-methyl-1,3,4-thiadiazol-5-ylthio)methyl]-8-oxo-5-thia-1-azabicyclo[4.2.0]oct-2-ene-2-carboxylic acid.

EXAMPLE 24

3-[(Acetyloxy)methyl]-7-[[2-[4-(chloromethyl)-phenyl]acetyl]-amino]-7-methoxy-8-oxo-5-thia-1-azabicyclo[4.2.0]oct-2-ene-2-carboxylic acid When in the procedure of Example 14 an appropriate amount of 3-[(acetyloxy)methyl]-7-amino-7-methoxy-8-oxo-5-thia-1-azabicyclo[4.2.0]oct-2-ene-2-carboxylic acid is substituted for 3-[(acetyloxy)methyl]-7-amino-8-oxo-5-thia-1-azabicyclo[4.2.0]oct-2-ene-2-carboxylic acid the title compound is obtained.

In a similar manner when an appropriate amount of 3-[(acetyloxy)methyl]-7-amino-7-methoxy-8-oxo-5-thia-1-azabicyclo4.2.0]oct-2-ene-2-carboxylic acid is reacted with the acid chloride listed in Table V the 7-methoxy derivatives of the respective cephalosporin derivatives listed in Table V are obtained.

EXAMPLE 25

3-[(Acetyloxy)methyl]-7-[[2-[4-(pyridiniummethyl)-phenyl]-acetyl]amino]-8-oxo-5-thia-1-azabicyclo[4.2.0-]oct-2-ene-2-carboxylic acid A mixture of 0.3 g of 3-[(acetyloxy)methyl]-7-[[2-[4-(chloromethyl)phenyl]acetyl]amino]-8-oxo-5-thia-1-azabicyclo4.2.0]oct-2-ene-2-carboxylic acid in 10 ml of pyridine was stirred at room temperature for 24 hours after which the excess pyridine was removed under high vacuum at room temperature yielding a yellow powder which was triturated with absolute ethanol to give 3-[(acetyloxy)methyl]-7-[[2-[4-(pyridiniummethyl)phenyl]acetyl]amino]-8-oxo-5-thia-1-azabicyclo[4.2.0]oct-2-ene-2-carboxylic acid. M.P. 102° C (dec.).

EXAMPLE 26

3-Methyl-7-[[2-[4-(pyridiniummethyl)phenyl]acetyl]-amino]-8-oxo-5-thia-1-azabicyclo[4.2.0]oct-2-ene-2-carboxylic acid When in the procedure of Example 25 0.3 g of 7-[[2-4-(chloromethyl)phenyl]acetyl]amino-3-methyl-8-oxo-5-thia-1-azabicyclo[4.2.0]oct-2-ene-2-carboxylic is substituted for 3-[(acetyloxy)methyl]-7-[[2-[4-(chloromethyl)phenyl]acetyl]-amino]-8-oxo-5-thia-1-azabicyclo[4.2.0]oct-2-ene-2-carboxylic acid the following product is obtained:

3-methyl-7-[[2-[4-(pyridiniummethyl)phenyl]acetyl]-amino]-8-oxo-5-thia-1-azabicyclo[4.2.0]oct-2-ene-2-carboxylic acid M.P. 102° C (dec.).

When in the procedure of Example 25 an appropriate amount of a chloromethyl substituted cephalosporin derivative listed in the following Table XI is substituted for 3-[(acetyloxy)-methyl]-7-[[2-[4-(chloromethyl)-phenyl]acetyl]amino]-8-oxo-5-thia-1-azabicyclo[4.2.0-]oct-2-ene-2-carboxylic acid the respective pryidinium-methyl substituted cephalosporin product listed in Table XI is obtained.

TABLE XI

| CHLOROMETHYL SUBSTITUTED CEPHALOSPORIN DERIVATIVE | PYRIDINIUMMETHYL SUBSTITUTED CEPHALOSPORIN PRODUCT |
|---|---|
| 3-[(acetyloxy)methyl-7-[[2-[4-(chloromethyl)-phenyl]-2-methylacetyl]-amino]-8-oxo-5-thia-a-azabicyclo[4.2.0]oct-2-ene-2-carboxylic acid | 3-[(acetyloxy)methyl]-7-[[2-[4-(pyridiniummethyl)phenyl]-2-methylacetyl]amino]-8-oxo-5-thia-1-azabicyclo[4.2.0]-oct-2-ene-2-carboxylic acid |
| 3-[(acetyloxy)methyl]-7-[[3-[4-(chloromethyl)-phenyl]propionyl]amino]-8-oxo-5-thia-1-azabicy-clo[4.2.0]oct-2-ene-2-carboxylic acid | 3-[(acetyloxy)methyl]-7-[[3-[4-(pyridiniummethyl)phenyl]-propionyl]amino]-8-oxo-5-thia-1-azabicyclo[4.2.0]oct-2-ene-2-carboxylic acid |
| 3-[(acetyloxy)methyl]-7-[[3-[4-(chloromethyl)-phenyl]-2-methylpropionyl]-amino]-8-oxo-5-thia-1-azabicyclo[4.2.0]oct-2-ene-2-carboxylic acid | 3-[(acetyloxy)methyl]-7-[[3-[4-(pyridiniummethyl)phenyl]-2-methylpropionyl]amino]-8-oxo-5-thia-1-azabicyclo[4.2.0]-oct-2-ene-2-carboxylic acid |
| 3-[(acetyloxy)methyl]-7-[[4-[4-(chloromethyl)-phenyl]butyryl]amino]-8-oxo-5-thia-1-azabicyclo-[4.2.0]oct-2-ene-2-carboxylic acid | 3-[(acetyloxy)methyl]-7-[[4-[4-(pyridiniummethyl)phenyl]-butyryl]amino]-8-oxo-5-thia-1-azabicyclo[4.2.0]oct-2-ene-2-carboxylic acid |
| 3-[(acetyloxy)methyl]-7-[[4-[4-(chloromethyl)-phenyl]-2-methylbutyryl]-amino]-8-oxo-5-thia-1-azabicyclo[4.2.0]oct-2-ene-2-carboxylic acid | 3-[(acetyloxy)methyl]-7-[[4-[4-(pyridiummethyl)phenyl]-2-methylbutyryl]amino]-8-oxo-5-thia-1-azabicyclo[4.2.0]-oct-2-ene-2-carboxylic acid |
| 3-[(acetyloxy)methyl]-7-[[2-[4-(chloromethyl)-phenoxy]acetyl]amino]-8-oxo-5-thia-1-azabicyclo-[4.2.0]oct-2-ene-2-carboxylic acid | 3-[(acetyloxy)methyl]-7-[[2-[4-(pyridiniummethyl)phenoxy]-acetyl]amino]-8-oxo-5-thia-1-azabicyclo[4.2.0]oct-2-ene-2-carboxylic acid |
| 3-[(acetyloxy)methyl]-7-[[2-[4-(chloromethyl)-phenoxy]-2-methylacetyl]-amino]-8-oxo-5-thia-1-azabicyclo[4.2.0]oct-2-ene-2-carboxylic acid | 3-[(acetyloxy)methyl]-7-[[2-[4-(pyridiniummethyl)phenoxy]-2-methylacetyl]amino]-8-oxo-5-thia-1-azabicyclo[4.2.0]-oct-2-ene-2-carboxylic acid |
| 3-[(acetyloxy)methyl]-7-[[4-[4-(chloromethyl)-phenoxy]butyryl]amino]-8-oxo-5-thia-1-azabicyclo-[4.2.0]oct-2-ene-2-carboxylic acid | 3-[(acetyloxy)methyl]-7-[[4-[4-(pyridiniummethyl)phenoxy]-butyryl]amino]-8-oxo-5-thia-1-azabicyclo[4.2.0]oct-2-ene-2-carboxylic acid |
| 3-[(acetyloxy)methyl]-7-[[4-[4-(chloromethyl)-phenoxy]-2-methylbutyryl]-amino]-8-oxo-5-thia-1-azabicyclo[4.2.0]oct-2-ene-2-carboxylic acid | 3-[(acetyloxy)methyl]-7-[[4-[4-(pyridiniummethyl)phenoxy]-2-methylbutyryl]amino]-8-oxo-5-thia-1-azabicyclo[4.2.0]-oct-2-ene-2-carboxylic acid |
| 3-[(acetyloxy)methyl]-7-[[3-[4-(chloromethyl)-phenoxy]propionyl]amino]-8-oxo-5-thia-1-azabicy-clo[4.2.0]oct-2-ene-2-carboxylic acid | 3-[(acetyloxy)methyl]-7-[[3-[4-(pyridiniummethyl)phenoxy]-propionyl]amino]-8-oxo-5-thia-1-azabicyclo[4.2.0]oct-2-ene-2-carboxylic acid |
| 3-[(acetyloxy)methyl[-7-[[2-[4-(chloromethyl)-anilino]acetyl]amino]-8-oxo-5-thia-1-azabicy-clo[4.2.0]oct-2-ene-2-carboxylic acid | 3-[(acetyloxy)methyl]-7-[[2-[4-(pyridiniummethyl)anilino]-acetyl]amino]-8-oxo-5-thia-1-azabicyclo[4.2.0]oct-2-ene-2-carboxylic acid |
| 3-[(acetyloxy)methyl]-7-[[2-[4-(chloromethyl)-anilino]-2-methylacetyl]-amino]-8-oxo-5-thia-1-azabicyclo[4.2.0]oct-2-ene-2-carboxylic acid | 3-[(acetyloxy)methyl]-7-[[2-[4-(pyridiummethyl)anilino]-2-methylacetyl]amino]-8-oxo-5-thia-1-azabicyclo[4.2.0]-oct-2-ene-2-carboxylic acid |
| 3-[)acetyloxy)methyl]-7-[[4-[4-(chloromethyl)- | 3-[(acetyloxy)methyl]-7-[[4-[4-(pyridiniummethyl)anilino]- |

TABLE XI-continued

| CHLOROMETHYL SUBSTITUTED CEPHALOSPORIN DERIVATIVE | PYRIDINIUMMETHYL SUBSTITUTED CEPHALOSPORIN PRODUCT |
|---|---|
| anilino]butyryl]amino]-8-oxo-5-thia-1-azabi-cyclo[4.2.0]oct-2-ene-2-carboxylic acid | butyryl]amino]-8-oxo-5-thia-1-azabicyclo[4.2.0]oct-2-ene-2-carboxylic acid |
| 3-[(acetyloxy)methyl]-7-[[3-[4-(chloromethyl)-anilino]-2-methylpro-pionyl]amino]-8-oxo-5-thia-1-azabicyclo[4.2.0]-oct-2-ene-2-carboxylic acid | 3-[(acetyloxy)methyl]-7-[[3-[4-(pyridiniummethyl)anilino]-2-methylpropionyl]amino]-8-oxo-5-thia-1-azabicyclo[4.2.0]-oct-2-ene-2-carboxylic acid |
| 3-[(acetyloxy)methyl]-7-[[2-[4-(chloromethyl)-phenylthio]acetyl]amino]-8-oxo-5-thia-1-azabicy-clo[4.2.0]oct-2-ene-2-carboxylic acid | 3-[(acetyloxy)methyl]-7-[[2-[4-(pyridiniummethyl)phenyl-thio]acetyl]amino]-8-oxo-5-thia-1-azabicyclo[4.2.0]oct-2-ene-2-carboxylic acid |
| 3-[(acetyloxy)methyl]-7-[[2-[4-(chloromethyl)-phenylthio]-2-methyl-acetyl]amino]-8-oxo-5-thia-1-azabicyclo[4.2.0]-oct-2-ene-2-carboxylic acid | 3-[(acetyloxy)methyl]-7-[[2-[4-(pyridiniummethyl)phenyl-thio]-2-methylacetyl]amino]-8-oxo-5-thia-1-azabicyclo-[4.2.0]oct-2-ene-2-carboxylic acid |
| 3-[(acetyloxy)methyl]-7-[[4-[4-(chloromethyl)-phenylthio]butyryl]-amino]-8-oxo-5-thia-1-azabicyclo[4.2.0]oct-2-ene-2-carboxylic acid | 3-[(acetyloxy)methyl]-7-[[4-[4-(pyridiniummethyl)phenyl-thio]butyryl]amino]-8-oxo-5-thia-1-azabicyclo[4.2.0]oct-2-ene-2-carboxylic acid |
| 3-[(acetyloxy)methyl]-7-[[2-[2-(chloro)-4-(chloro-methyl)phenyl]acetyl]-amino]-8-oxo-5-thia-1-azabicyclo[4.2.0]oct-2-ene-2-carboxylic acid | 3-[(acetyloxy)methyl]-7-[[2-[2-(chloro)-4-(pyridinium-methyl)phenyl]acetyl]amino]-8-oxo-5-thia-1-azabicyclo-[4.2.0]oct-2-ene-2-carboxylic acid |
| 3-[(acetyloxy)methyl]-7-[[2-[5-(chloromethyl)-2-thienyl]acetyl]amino]-8-oxo-5-thia-1-azabicyclo-[4.2.0]oct-2-ene-2-car-boxylic acid | 3-[(acetyloxy)methyl]-8-[[2-[5-(pyridiniummethyl)-2-thi-enyl]-acetyl]amino]-8-oxo-5-thia-1-azabicyclo[4.2.0]oct-2-ene-2-carboxylic acid |
| 3-[(acetyloxy)methyl[-7-[[2-[2-(chloromethyl)-4-methoxyphenyl]-2-hydroxy-acetyl]amino]8-oxo-5-thia-1-azabicyclo[4.2.0]-oct-2-ene-2-carboxylic acid | 3-[(acetyoxy)methyl]-7-[[2-[2-(pyridiniummethyl)-4-methoxyphenyl]-2-hydroxyace-tyl]amino]-8-oxo-5-thia-1-azabicyclo[4.2.0]oct-2-ene-2-carboxylic acid |
| 3-[(acetyloxy)methyl]-7-[[2-[4-(chloromethyl)-phenyl]-2-hydroxyacetyl]-2-hydroxyacetyl]amino]-8-oxo-amino]-8-oxo-5-thia-1-azabicyclo[4.2.0]oct-2-ene-2-carboxylic acid | 3-[(acetyloxy)methyl]-7-[[2-4-(pyridiniummethyl)phenyl]-

5-thia-1-azabicyclo[4.2.0]-oct-2-ene-2-carboxylic acid |
| 3-[(acetyloxy)methyl]-7-[[3-[4-(chloromethyl)-phenyl]-2-hydroxypropi-onyl]amino]-8-oxo-5-thia-1-azabicyclo[4.2.0]oct-2-ene-2-carboxylic acid | 3-[(acetyloxy)methyl]-7-[[3-[4-(pyridiniummethyl)phenyl]-2-hydroxypropionyl]amino]-8-oxo-5-thia-1-azabicyclo-[4.2.0]oct-2-ene-2-carbox-ylic acid |
| 3-[(acetyloxy)methyl]-7-[[3-[4-(chloromethyl)-phenyl]-2-hydroxybutyryl]-amino]-8-oxo-5-thia-1-azabicyclo[4.2.0]oct-2-ene-2-carboxylic acid | 3-[(acetyloxy)methyl]-7-[[3-[4-(pyridiniummethyl)-phenyl]-2-hydroxybutyryl]amino]-8-oxo-5-thia-1-azabicyclo-[4.2.0]oct-2-ene-2-carbox-ylic acid |
| 3-[ (acetyloxy)methyl]-7-[[3-[4-(chloromethyl)-phenoxy]-2-hydroxypro-pionyl]amino]-8-oxo-5-thia-1-azabicyclo[4.2.0]-oct-2-ene-2-carboxylic acid | 3-[(acetyloxy)methyl]-7-[[3-[4-(pyridiniummethyl)phenoxy]-2-hydroxypropionyl]amino]-8-oxo-5-thia-1-azabicyclo-[4.2.0]oct-2-ene-2-carboxylic acid |
| 3-[(acetyloxy)methyl]-7-[[2-[5-(chloromethyl)-2-thienyl]-2-hydroxy-acetyl]amino]-8-oxo-5-thia-1-azabicyclo[4.2.0]-oct-2-ene-2-carboxylic acid | 3-[(acetyloxy)methyl]-7-[[2-[5-(pyridiniummethyl)-2-thi-enyl]-2-hydroxyacetyl]amino]-8-oxo-5-thia-1-azabicyclo-[4.2.0]oct-2-ene-2-carboxylic acid |
| 3-[(acetyloxy)methyl]-7-[[2-[4-(chloromethyl)-phenyl]-2-carboxyacetyl]-amino]-8-oxo-5-thia-1-azabicyclo[4.2.0]oct-2-ene-2-carboxylic acid | 3-[(acetyloxy)methyl]-7-[[2-[4-(pyridiniummethyl)-phenyl]-2-carboxyacetyl]amino]-8-oxo-5-thia-1-azabicyclo[4.2.0]-oct-2-ene-2-carboxylic acid |
| 3-[(acetyloxy)methyl]-7- | 3-[(acetyloxy)methyl]-7-[[2- |

TABLE XI-continued

| CHLOROMETHYL SUBSTITUTED CEPHALOSPORIN DERIVATIVE | PYRIDINIUMMETHYL SUBSTITUTED CEPHALOSPORIN PRODUCT |
|---|---|
| [[2-[4-(chloromethyl)-phenyl]-2-sulfoacetyl]-amino]-8-oxo-5-thia-1-azabicyclo[4.2.0]oct-2-ene-2-carboxylic acid | [4-(pyridiniummethyl)phenyl]-2-sulfoacetyl]amino]-8-oxo-5-thia-1-azabicyclo[4.2.0]oct-2-ene-2-carboxylic acid |
| 3-[(acetyloxy)methyl]-7-[[4-[4-(chloromethyl)-phenyl]-2-sulfobutyryl]-amino]-8-oxo-5-thia-1-azabicyclo[4.2.0]oct-2-ene-2-carboxylic acid | 3-[(acetyloxy)methyl]-7-[[4-[4-(pyridiniummethyl)phenyl]-2-sulfobutyryl]amino]-8-oxo-5-thia-1-azabicyclo[4.2.0]oct-2-ene-2-carboxylic acid |
| 3-[(acetyloxy)methyl]-7-[[3-[4-(chloromethyl)-phenyl]-2-carboxypropionyl]amino]-8-oxo-5-thia-1-azabicyclo[4.2.0]oct-2-ene-2-carboxylic acid | 3-[(acetyloxy)methyl]-7-[[3-[4-(pyridiniummethyl)phenyl]-2-carboxypropionyl]amino]-8-oxo-5-thia-1-azabicyclo[4.2.0] -oct-2-ene-2-carboxylic acid |
| 3-[(acetyloxy)methyl]-7-[[4-[4-(chloromethyl)-phenoxy]-2-carboxybutyryl]-amino]-8-oxo-5-thia-1-azabicyclo[4.2.0]oct-2-ene-2-carboxylic acid | 3-[(acetyloxy)methyl]-7-[[4-[4-(pyridiniummethyl)phenoxy]-2-carboxybutyryl]amino]-8-oxo-5-thia-1-azabicyclo[4.2.0]oct-2-ene-2-carboxylic acid |
| 3-[(acetyloxy)methyl]-7-[[4-[4-(chloromethyl)-phenylthio]-2-carboxybutyryl]amino]-8-oxo-5-thia-1-azabicyclo[4.2.0]oct-2-ene-2-carboxylic acid | 3-[(acetyloxy)methyl]-7-[[4-[4-(pyridiniummethyl)phenylthio]-2-carboxybutyryl]amino]-8-oxo-5-thia-1-azabicyclo[4.2.0]oct-2-ene-2-carboxylic acid |
| 3-[(acetyloxy)methyl]-7-[[3-[4-(chloromethyl)-anilino]-2-carboxypropionyl]amino]-8-oxo-5-thia-1-azabicyclo[4.2.0]oct-2-ene-2-carboxylic acid | 3-[(acetyloxy)methyl]-7-[[3-[4-(pyridiniummethyl)anilino]-4-(pyridiniummethyl)phenyl]amino]-8-oxo-5-thia-1-azabicyclo[4.2.0]-oct-2-ene-2-carboxylic acid |
| 3-[(acetyloxy)methyl]-7-[[3-[5-(chloromethyl)-2-thienyl]-2-carboxypropionyl]amino]-8-oxo-5-thia-1-azabicyclo[4.2.0]oct-2-ene-2-carboxylic acid | 3-[(acetyloxy)methyl]-7-[[3-[5-(pyridiniummethyl)-2-thienyl]-2-carboxypropionyl]amino]-8-oxo-5-thia-1-azabicyclo[4.2.0]oct-2-ene-2-carboxylic acid |
| 3-[(acetyloxy)methyl]-7-[[2-[4-(chloromethyl)-phenyl]acetyl]amino]-8-oxo-5-thia-1-azabicyclo[4.2.0]oct-2-ene-2-carboxylic acid | 3-[(acetyloxy)methyl]-7-[[2-[4-(pyridiniummethyl)phenyl]acetyl]amino]-8-oxo-5-thia-1-azabicyclo[4.2.0]oct-2-ene-2-carboxylic acid pivaloyloxymethyl ester |
| 3-[(acetyloxy)methyl]-7-[[2-[4-(chloromethyl)-phenyl]-2-methylacetyl]-amino]-8-oxo-5-thia-1-azabicyclo[4.2.0]oct-2-ene-2-carboxylic acid propionyloxymethyl ester | 3-[(acetyloxy)methyl]-7-[[ 2-[4-(pyridiniummethyl)phenyl] -2-methylacetyl]amino]-8-oxo-5-thia-1-azabicyclo[4.2.0]-oct-2-ene-2-carboxylic acid propionyloxymethyl ester |
| 3-[(acetyloxy)methyl]-7-[[3-[4-(chloromethyl)-phenyl]-2-methylpropionyl]-amino]-8-oxo-5-thia-1-azabicyclo[4.2.0]oct-2-ene-2-carboxylic acid acetyloxymethyl ester | 3-[(acetyloxy)methyl]-7-[[3-[4-(pyridiniummethyl)phenyl]-2-methylpropionyl]amino]-8-oxo-5-thia-1-azabicyclo[4.2.0]oct-2-ene-2-carboxylic acid acetyloxymethyl ester |
| 3-[(acetyloxy)methyl]-7-[[4-[4-(chloromethyl)-phenyl]-2-methylbutyryl]-amino]-8-oxo-5-thia-1-azabicyclo[4.2.0]oct-2-ene-2-carboxylic acid butyryloxymethyl ester | 3-[(acetyloxy)methyl]-7-[[4-[4-(pyridiniummethyl)phenyl]-2-methylbutyryl]amino]-8-oxo-5-thia-1-azabicyclo[4.2.0]-oct-2-ene-2-carboxylic acid butyryloxymethyl ester |
| 3-[(acetyloxy)methyl]-7-[[2-[4-(chloromethyl)-phenoxy]-2-methylacetyl]-amino]-8-oxo-5-thia-1-azabicyclo[4.2.0]oct-2-ene-2-carboxylic acid 2-amino-3-methylbutyryloxymethyl ester | 3-[(acetyloxy)methyl]-7-[[2-[4-(pyridiniummethyl)phenyl]-2-methylacetyl]amino]-8-oxo-5-thia-1-azabicyclo[4.2.0]oct-2-ene-2-carboxylic acid 2-amino-3-methylbutyryloxymethyl ester |
| 3-[(acetyloxy)methyl]-7-[[4-[4-(chloromethyl)-phenoxy]-2-methylbutyryl]-amino]-8-oxo-5-thia-1-azabicyclo[4.2.0]oct-2-ene-2-carboxylic acid N-ethoxycarbonyl-N-methyl-aminoethyl ester | 3-[(acetyloxy)methyl]-7-[[4-[4-(pyridiniummethyl)phenyl]-2-methylbutyryl]amino]-8-oxo-5-thia-1-azabicyclo[4.2.0]-oct-2-ene-2-carboxylic acid N-ethoxycarbonyl-N-methyl-aminoethyl ester |
| 3-[(acetyloxy)methyl]-7- | 3-[(acetyloxy)methyl]-7-[[2- |
| [[2-[4-(chloromethyl)-anilino]acetyl]amino]-8-oxo-5-thia-1-azabicyclo-[4.2.0]oct-2-ene-carboxylic acid N-methyl-N-propionylaminomethyl ester | [4-(pyridiniummethyl)anilino]-acetyl]amino]-8-oxo-5-thia-1-azabicyclo[4.2.0]oct-2-ene-2-carboxylic acid N-methyl-N-propionylaminoethyl ester |
| 3-[(acetyloxy)methyl]-7-[[4-[4-(chloromethyl)-anilino]butyryl]amino]-8-oxo-5-thia-1-azabicyclo[4.2.0]oct-2-ene-2-carboxylic acid N-butyryl-aminomethyl ester | 3-[(acetyloxy)methyl]-7-[[4-[4-(pyridiniummethyl)anilino]-butyryl]amino]-8-oxo-5-thia-1-azabicyclo[4.2.0]-oct-2-ene-2-carboxylic acid N-butyryl-aminomethyl ester |
| 3-[(acetyloxy)methyl]-7-[[2-[4-(chloromethyl)-phenylthio]acetyl]amino]-8-oxo-5-thia-1-azabicyclo[4.2.0]oct-2-ene-2-carboxylic acid N-acetyl-aminomethyl ester | 3-[(acetyloxy)methyl]-7-[[2-[4-(pyridiniummethyl)phenyl-thio]acetyl]amino]-8-oxo-5-thia-1-azabicyclo[4.2.0]oct-2-ene-carboxylic acid N-acetylaminomethyl ester |
| 3-[(acetyloxy)methyl]-7-[[4-[4-(chloromethyl)-phenylthio]butyryl]amino]-8-oxo-5-thia-1-azabicyclo[4.2.0]oct-2-ene-2-carboxylic acid N-methyl-N-ethoxycarbonylaminomethyl ester | 3-[(acetyloxy)methyl]-7-[[4-[4-(pyridiniummethyl)phenyl-thio]butyryl]amino]-8-oxo-5-thia-1-azabicyclo[4.2.0]-oct-2-ene-carboxylic acid N-methyl-N-ethoxycarbonyl-aminomethyl ester |
| 3-[(acetyloxy)methyl]-7-[[2-[5-(chloromethyl)-2-thienyl]acetyl]amino]-8-oxo-5-thia-1-azabicyclo-[4.2.0]oct-2-ene-2-carboxylic acid p-pivalyloxy-benzyl ester | 3-[(acetyloxy)methyl]-7-[[2-[5-(pyridiniummethyl)-2-thienyl]acetyl]amino]-8-oxo-5-thia-1-azabicyclo[4.2.0]oct-2-ene-2-carboxylic acid p-pivalyloxybenzyl ester |
| 3-[(acetyloxy)methyl]-7-[[2-[4-(chloromethyl)-phenyl]-2-hydroxyacetyl]-amino]-8-oxo-5-thia-1-azabicyclo[4.2.0]oct-2-ene-2-carboxylic acid p-(propionyloxy)benzyl ester | 3-[(acetyloxy)methyl]-7-[[2-[4-(pyridiniummethyl)-phenyl]-2-hydroxyacetyl]amino]-8-oxo-5-thia-1-azabicyclo[4.2.0]-oct-2-ene-2-carboxylic acid p-(propionyloxy)benzyl ester |
| 3-[(acetyloxy)methyl]-7-[[4-[4-(chloromethyl)-phenyl]-2-hydroxybutyryl]-amino]-8-oxo-5-thia-1-azabicyclo[4.2.0]oct-2-ene-2-carboxylic acid p-(acetyloxy)benzyl ester | 3-[(acetyloxy)methyl]-7-[[4-[4-(pyridiniummethyl)phenyl]-2-hydroxybutyryl]amino]-8-oxo-5-thia-1-azabicyclo[4.2.0]-oct-2-ene-2-carboxylic acid p-(acetyloxy)benzyl ester |
| 3-[(acetyloxy)methyl]-7-[[2-[5-(chloromethyl)-2-thienyl]-2-hydroxyacetyl]-amino]-8-oxo-5-thia-1-azabicyclo[4.2.0]oct-2-ene-2-carboxylic acid p-(val-yryloxy)benzyl ester | 3-[(acetyloxy)methyl]-7-[[2-[5-(pyridiniummethyl)-2-thienyl]-2-hydroxyacetyl]amino]-8-oxo-5-thia-1-azabicyclo-[4.2.0]oct-2-ene-2-carboxylic acid p-valyryloxy)benzyl ester |
| 3-[(2-methyl-1,3,4,-thiadiazol-5-ylthio)methyl]-7-[[2-[4-(chloromethyl)phenyl]acetyl]amino]-8-oxo-5-thia-1-azabicyclo[4.2.0]-oct-2-ene-2-carboxylic acid | 3-[(2-methyl-1,3,4-thiadiazol-5-ylthio)methyl]-7-[[2-[4-pyridiniummethyl)phenyl]acetyl]amino]-8-oxo-5-thia-1-azabicyclo[4.2.0]oct-2-ene-2-carboxylic acid |
| 3-[(1,3,4-thiadiazol-5-ylthio)methyl]-7-[[2-[4-(chloromethyl)phenoxy]-acetyl]amino]-8-oxo-5-thia-1-azabicyclo[4.2.0]-oct-2-ene-2-carboxylic acid | 3-[(1,3,4-thiadiazol-5-ylthio)-methyl]-7-[[2-[4-(pyridinium-methyl)phenoxypacetyl]amino]-8-oxo-5-thia-1-azabicyclo-[4.2.0]oct-2-ene-2-carboxylic acid |
| 3-[(3-methyl-1,2,4-thiadiazol-5-ylthio)methyl]-7-[[3-[4-(chloromethyl)-phenyl] propionyl]amino]-8-oxo-5-thia-1-azabicyclo[4.2.0]oct-2-ene-2-carboxylic acid | 3-[(3-methyl-1,2,4-thiadiazol-5-ylthio)methyl]-7-[[3-[4-(pyridiniummethyl)phenyl]propionyl]amino]-8-oxo-5-thia-1-azabicylo[4.2.0]oct-2-ene-2-carboxylic acid |
| 3-[(tetrazol-5-ylthio)-methyl]-7-[[4-[4-(chloromethyl)phenyl]butyryl]-amino]-8-oxo-5-thia-1-azabicyclo[4.2.0]oct-2-ene-2-carboxylic acid | 3-[(tetrazol-5-ylthio)methyl]-7-[[4-[4-(pyridiniummethyl)-phenyl]butyryl]amino]-8-oxo-5-thia-1-azabicyclo[4.2.0]-oct-2-ene-2-carboxylic acid |
| 3-[(1-methyltetrazol-5-yl-thio)methyl]-7-[[2-[4-(chloromethyl)phenyl]ace-tyl]amino]-8-oxo-5-thia-1- | 3-[(1-methyltetrazol-5-ylthio)-methyl]-7-[[2-[4-(pyridinium-methyl)phenyl]acetyl]amino]-8-oxo-5-thia-1-azabicyclo- |

TABLE XI-continued

| CHLOROMETHYL SUBSTITUTED CEPHALOSPORIN DERIVATIVE | PYRIDINIUMMETHYL SUBSTITUTED CEPHALOSPORIN PRODUCT |
|---|---|
| azabicyclo[4.2.0]oct-2-ene-2-carboxylic acid | [4.2.0]oct-2-ene-2-carboxylic acid |
| 3-[(2-methyl-1,3,4-oxadiazol-5-ylthio)methyl]-7-[[4-[4-(chloromethyl)phenyl]butyryl]amino]-8-oxo-5-thia-1-azabicyclo[4.2.0]-oct-2-ene-2-carboxylic acid | 3-[(2-methyl-1,3,4-oxadiazol-5-ylthio)methyl]-7-[[4-[4-(pyridiniummethyl)phenyl]butyryl]amino]-8-oxo-5-thia-1-azabicyclo[4.2.0]oct-2-ene-2-carboxylic acid |
| 3-[(3-methyl-1,2,4-thiadiazol-5-ylthio)methyl]-7-[[3-[4-(chloromethyl)phenoxy]propionyl]amino]-8-oxo-5-thia-1-azabicyclo[4.2.0]oct-2-end-2-carboxylic acid propionyloxymethyl ester | 3-[(3-methyl-1,2,4-thiadiazol-5-ylthio)methyl]-7-[[3-[4-(pyridiniummethyl)phenoxy]propionyl]amino]-8-oxo-5-thia-1-azabicyclo[4.2.0]oct-2-ene-2-carboxylic acid propionyloxymethyl ester |
| 3-[(1-methyltetrazol-5-ylthio)methyl]-7-[[2-[4-(chloromethyl)anilino]-2-methylacetyl]amino]-8-oxo-5-thia-1-azabicyclo-[4.2.0]oct-2-ene-2-carboxylic acid pivalyloxymethyl ester | 3-[(1-methyltetrazol-5-ylthio)methyl]-7-[[2-[4-(pyridiniummethyl)anilino]-2-methylacetyl]amino]-8-oxo-5-thia-1-azabicyclo[4.2.0]-oct-2-ene-2-carboxylic acid pivalyloxymethyl ester |
| 3-[(1,3,4-thiadiazol-5-ylthio)methyl]-7-[[3-[4-(chloromethyl)anilino]-2-methylpropionyl]amino]-8-oxo-5-thia-1-azabicyclo[4.2.0]oct-2-ene-2-carboxylic acid acetyloxymethyl ester | 3-[(1,3,4-thiadiazol-5-ylthio)methyl]-7-[[3-[4-pyridiniummethyl)anilino]-2-methylpropionyl]amino]-8-oxo-5-thia-1-azabicyclo[4.2.0]oct-2-ene-2-carboxylic acid acetyloxymethyl ester |
| 3-[(tetrazol-5-ylthio)methyl]-7-[[2-[4-(chloromethyl)phenylthio]-2-methylacetyl]amino]-8-oxo-5-thia-1-azabicyclo[4.2.0]oct-2-ene-2-carboxylic acid butyryloxymethyloxymethyl ester | 3-[(tetrazol-5-ylthio)methyl]-7-[[2-[4-(pyridiniummethyl)phenylthio]-2-methylacetyl]amino]-8-oxo-5-thia-1-azabicyclo[4.2.0]oct-2-ene-2-carboxylic acid butyryloxymethyl ester |
| 3-[(2-methyl-1,3,4-oxadiazol-5-ylthio)methyl]-7-[[2-[2-(chloro)-4-(chloromethyl)phenyl]acetyl]amino]-8-oxo-5-thia-1-azabicyclo-[4.2.0]oct-2-ene-2-carboxylic acid 2-amino-3-methylbutyryloxymethyl ester | 3-[(2-methyl-1,3,4-oxadiazol-5-ylthio)methyl]-7-[[2-[2-(chloro)-4-(pyridiniummethyl)-phenyl]acetyl]amino]-8-oxo-5-thia-1-azabicyclo[4.2.0]-oct-2-ene-2-carboxylic acid 2-amino-3-methylbutyryloxymethyl ester |
| 3-[(2-methyl-1,3,4-thiadiazol-5-ylthio)methyl]-7-[[2-[2-(chloromethyl)-4-methoxyphenyl]-2-hydroxyacetyl]amino]-8-oxo-5-thia-1-azabicyclo-[4.2.0]oct-2-ene-2-carboxylic acid N-ethoxycarbonyl-N-methylaminomethyl ester | 3-[(2-methyl-1,3,4-thiadiazol-5-ylthio)methyl]-7-[[2-[2-(pyridiniummethyl)-4-methoxyphenyl]-2-hydroxyacetyl]amino]-8-oxo-5-thia-1-azabicyclo[4.2.0]oct-2-ene-2-carboxylic acid N-ethoxycarbonyl-N-methylaminomethyl ester |
| 3-[(1-methyltetrazol-5-ylthio)methyl]-7-[[3-[4-(chloromethyl)phenyl]-2-hydroxypropionyl]amino]-8-oxo-5-thia-1-azabicyclo[4.2.0]oct-2-ene-2-carboxylic acid p-pivalyloxybenzyl ester | 3-[(1-methyltetrazol-5-ylthio)methyl]-7-[[3-[4-pyridiniummethyl)phenyl[-2-hydroxypropionyl]amino]-8-oxo-5-thia-1-azabicyclo[4.2.0]oct-2-ene-2-carboxylic acid p-pivalyloxybenzyl ester |
| 7-[[2-[4-(chloromethyl)phenyl]-2-(carboxyacetyl)amino]-3-[(2-methyl-1,3,4-thiadiazol-5-ylthio)methyl]-8-oxo-5-thia-1-azabicyclo[4.2.0]oct-2-ene-2-carboxylic acid | 7-[[2-[4-(pyridiniummethyl)phenyl]-2-carboxyacetyl]amino]-3-[(2-methyl-1,3,4-thiadiazol-5-ylthio)methyl]-8-oxo-5-thia-1-azabicyclo[4.2.0]oct-2-ene-2-carboxylic acid |
| 7-[[2-[4-(chloromethyl)pheyl]-2-sulfoacetyl]amino]-2-[(1,3,4-thiadiazol-5-ylthio)methyl]-8-oxo-5-thia-1-azabicyclo[4.2.0]oct-2-ene-2-carboxylic acid | 7-[[2-[4-(pyridiniummethyl)phenyl]-2-sulfoacetyl]amino]-3-[(1,3,4-thiadiazol-5-ylthio)methyl]-8-oxo-5-thia-1-azabicyclo[4.2.0]-oct-2-ene-2-carboxylic acid |
| 7-[[4-[4-(chloromethyl)phenyl]-2-sulfobutyryl]amino]-3-[(3-methyl-1,2,-4-thiadiazol-5-ylthio)methyl]-8-oxo-5-thia-1-azabicyclo[4.2.0]oct-2- | 7-[[4-[4-(pyridiniummethyl)-2-sulfobutyryl]amino]-3-[(3-methyl-1,2,4-thiadiazol-5-ylthio)methyl]-8-oxo-5-thia-1-azabicyclo[4.2.0]oct-ene-2-carboxylic acid |
| 7-[[4-[4-(chloromethyl)phenoxy]-2-carboxybu- | 7-[[4-[4-(pyridiniummethyl)phenoxy]-2-carboxybutyryl]- |

TABLE XI-continued

| CHLOROMETHYL SUBSTITUTED CEPHALOSPORIN DERIVATIVE | PYRIDINIUMMETHYL SUBSTITUTED CEPHALOSPORIN PRODUCT |
|---|---|
| tyryl]amino]-3-[(tetrazol-5-ylthio)methyl]-8-oxo-5-thia-1-azabicyclo-[4.2.0]oct-2-ene-2-carboxylic acid | amino]-3-[(tetrazol-5-ylthio)-methyl]-8-oxo-5-thia-1-azabicyclo[4.2.0]oct-2-ene-2-carboxylic acid |
| 7-[[3-[4-(chloromethyl)-anilino]-2-carboxypropionyl]amino]-3-[1-methyltetrazol-5-ylthio)-methyl]-8-oxo-5-thia-1-azabicyclo[4.2.0]oct-2-ene-2-carboxylic acid | 7-[[3-[4-(pyridiniummethyl)-anilino]-2-carboxypropionyl]-amino]-3-[(1-methyltetrazol-5-ylthio)methyl]-8-oxo-5-thia-1-azabicyclo[4.2.0]oct-2-ene-2-carboxylic acid |
| 7-[[3-[5-(chloromethyl)-2-thienyl]-2-carboxypropionyl]amino]-3-[(2-methyl-1,3,4-oxadiazol-5-ylthio)methyl]-8-oxo-5-thia-1-azabicyclo-[4.2.0]oct-2-ene-2-carboxylic aicd | 7-[[3-[5-(pyridiniummethyl)-2-thienyl]-2-carboxypropionyl]-amino]-3-[(2-methyl-1,3,4-oxadiazol-5-ylthio)methyl]-8-oxo-5-thia-1-azabicyclo[4.2.0]-oct-2-ene-2-carboxylic acid |
| 3-[(acetyloxy)methyl]-7-[[2-[4-(chloromethyl)-phenyl]-2-carboxyacetyl]-amino-8-oxo-5-thia-1-azabicyclo[4.2.0]oct-2-ene-2-carboxylic acid propionyloxymethyl ester | 3-[(acetyloxy)methyl]-7-[[2-[4-(pyridiniummethyl)phenyl]-2-carboxyacetyl]amino]-8-oxo-5-thia-1-azabicyclo[4.2.0]oct-2-ene-2-carboxylic acid propionyloxymethyl ester |
| 7-[[2-[4-(chloromethyl)-phenyl]-2-carboxyacetyl]-amino]-3-[(2-methyl-1,3,4-thiadiazol-5-ylthio)-methyl]-8-oxo-5-thia-1-azabicyclo[4.2.0]oct-2-ene-2-carboxylic acid | 7-[[2-[4-(pyridiniummethyl)-phenyl]-2-carboxyacetyl]amino]-3-[(2-methyl-1,3,4-thiadiazol-5-ylthio)methyl]-8-oxo-5-thia-1-azabicyclo[4.2.0]oct-2-ene-2-carboxylic acid |
| 3-[(acetyloxy)methyl]-7-[[2-[4-(chloromethyl)-phenyl]acetyl]amino]-7-methoxy-8-oxo-5-thia-1-azabicyclo[4.2.0]oct-2-ene-2-carboxylic acid | 3-[(acetyloxy)methyl]-7-[[2-[4-(pyridiniummethyl)phenyl]-acetyl]amino]-7-methoxy-8-oxo-5-thia-1-azabicyclo[4.2.0]oct-2-ene-2-carboxylic acid |

EXAMPLE 27

3-[(Acetyloxy)methyl]-7-[[2-[4-(pyridiniummethyl)-phenyl]-2-aminoacetyl]amino]-8-oxo-5-thia-1-azabicyclo[4.2.0]oct-2-ene-2-carboxylic acid (A) A mixture of 7.5 g of 3-[(acetyloxy)methyl]-7-[[2-[4-(chloromethyl)phenyl]-2-aminoacetyl]amino]-8-oxo-5-thia-1-azabicyclo[4.2.0]oct-2-ene-2-carboxylic acid and 200 ml of pyridine is stirred at room temperature for 24 hours after which the solvent is removed in vacuo at room temperature. The product is triturated with 2:1 benzene-acetone to give the amine pyridiniummethyl derivative.

(B) At 0° C 10 ml of trifluoroacetic acid is added to 5g of 3-[(acetyloxy)methyl]-7-[[2-[4-(pyridiniummethyl)-phenyl]-2-aminoacetyl]amino]-8-oxo-5-thia-1-azabicyclo[4.2.0]oct-2-ene-2-carboxylic acid wherein the 2-amino group is protected with tert-butoxycarbonyl obtained in (a) above. The mixture is stirred for several minutes under a nitrogen atmosphere at room temperature. The excess trifluoroacetic acid is removed in vacuo and the remaining residue is triturated with diethylether then dissolved in 175 ml of water. The solution is filtered and the pH of the filtrate adjusted to 5.5 by adding Amberlite IR4B resin that has been washed several times with water. The resin is filtered off and the water concentrated in vacuo. A precipitate forms from the concentrate which is removed and washed with ethanol to give 3-[(acetyloxy)methyl]-7-[[2-[4-(pyridiniummethyl)phenyl]-2-aminoacetyl]amino]-8-oxo-5-thia-1-azabicyclo[4.2.0]oct-2-ene-2-carboxylic acid.

In a similar manner when appropriate amounts of chloromethylated derivatives listed in the following Table XII are reacted with pyridine as in Example 28(A) and the resulting product subsequently treated as in Example 28(B), the respective pyridiniummethyl substituted cephalosporin products listed in Table XII are obtained.

TABLE XII

| CHLOROMETHYL SUBSTITUTED CEPHALOSPORIN DERIVATIVE | PYRIDINIUMMETHYL SUBSTITUTED CEPHALOSPORIN DERIVATIVE |
|---|---|
| 3-[(acetyloxy)methyl]-7-[[3-[4-(chloromethyl)phenyl]-2-aminopropionyl]amino]-8-oxo-5-thia-1-azabicyclo[4.2.0]-oct-2-ene-2-carboxylic acid | 3-[(acetyloxy)methyl-7-[[3-[4-(pyridiniummethyl)phenyl]-2-aminopropionyl]amino]-8-oxo-5-thia-1-azabicyclo-[4.2.0]oct-2-ene-2-carboxylic acid |

| CHLOROMETHYL SUBSTITUTED CEPHALOSPORIN DERIVATIVE | PYRIDINIUMMETHYL SUBSTITUTED CEPHALOSPORIN PRODUCT |
|---|---|
| 3-[(acetyloxy)methyl]-7-[[4-[4-(chloromethyl)-phenyl]-2-aminobutyryl]amino]-8-oxo-5-thia-1-azabicyclo[4.2.0]oct-2-ene-2-carboxylic acid | 3-[(acetyloxy)methyl]-7-[[4-[4-(pyridiniummethyl)phenyl]-2-aminobutyryl]amino]-8-oxo-5-thia-1-azabicyclo[4.2.0]oct-2-ene-2-carboxylic acid |
| 3-[(acetyloxy)methyl]-7-[[4-[4-(chloromethyl)-phenoxy]-2-aminobutyryl]amino]-8-oxo-5-thia-1-azabicyclo[4.2.0]oct-2-ene-2-carboxylic acid | 3-[(acetyloxy)methyl]-7-[[4-[4-(pyridiniummethyl)phenoxy]-2-aminobutyryl]amino]-8-oxo-5-thia-1-azabicyclo[4.2.0]-oct-2-ene-2-carboxylic acid |
| 3-[(acetyloxy)methyl]-7-[[3-[4-(chlorometyl)-phenoxy]-2-aminopropionyl]amino]-8-oxo-5-thia-1-azabicyclo[4.2.0]oct-2-ene-2-carboxylic acid | 3-[(acetyloxy)methyl]-7-[[3-[4-(pyridiniummethyl)phenoxy]-2-aminopropionyl]amino]-8-oxo-5-thia-1-azabicyclo[4.2.0]-oct-2-ene-2-carboxylic acid |
| 3-[(acetyloxy)methyl]-7-[[4-[4-(chloromethyl)-anilino]-2-aminobutyryl]-8-oxo-5-thia-1-azabicyclo[4.2.0]oct-2-ene-2-carboxylic acid | 3-[(acetyloxy)methyl]-7-[[4-[4-(pyridiniummethyl)anilino]-2-aminobutyrl[-8-oxo-5-thia-1-azabicyclo[4.2.0]oct-2-ene-2-carboxylic acid |
| 3-[(acetyloxy)methyl]-7-[[4-[4-(chloromethyl)-phenylthiol]-2-aminobutyryl]amino]-8-oxo-5-thia-1-azabicyclo[4.2.0]-oct-2-ene-2-carboxylic acid | 3-[(acetyloxy)methyl]-7-[[4-[4-(pyridiniummethyl)phenylthio]-2-aminobutyryl]amino]-8-oxo-5-thia-1-azabicyclo-[4.2.0]oct-2-ene-2-carboxylic acid |
| 3-[(acetyloxy)methyl]-7-[[3-[4-(chloromethyl)-phenylthio]-2-aminopropionyl]amino]-8-oxo-5-thia-1-azabicyclo[4.2.0]-oct-2-ene-2-carboxylic acid | 3-[(acetyloxy)methyl]-7-[[3-[4-(pyridiniummethyl)phenylthio]-2-aminopropionyl]amino]-8-oxo-5-thia-1-azabicyclo-[4.2.0]oct-2-ene-2-carboxylic acid |
| 3-[(acetyloxy)methyl]-7-[[2-[5-(chloromethyl)-2-thienyl]-2-aminoacetyl]-amino]-8-oxo-5-thia-1-azabicyclo[4.2.0]oct-2-ene-2-carboxylic acid | 3-[(acetyloxy)methyl]-7-[[2-[5-(pyridiniummethyl)-2-thienyl]-2-aminoacetyl]amino]-8-oxo-5-thia-1-azabicyclo[4.2.0]-oct-2-ene-2-carboxylic acid |
| 3-[(acetyloxy)methyl]-7-[[3-[5-(chloromethyl)-2-thienyl]-2-aminopropionyl]-amino]-8-oxo-5-thia-1-azabicyclo[4.2.0]oct-2-ene-2-carboxylic acid | 3-[(acetyloxy)methyl]-7-[[3-[5-(pyridiniummethyl)-2-thienyl]-2-aminopropionyl]amino]-8-oxo-5-thia-1-azabicyclo-[4.2.0]oct-2-ene-2-carboxylic acid |
| 3-[(acetyloxy)methyl]-7-[[4-[5-(chloromethyl)-2-thienyl]-2-aminobutyryl]-amino]-8-oxo-5-thia-1-azabicyclo[4.2.0]oct-2-ene-2-carboxylic acid | 3-[(acetyloxy)methyl]-7-[[4-[5-(pyridiniummethyl)-2-thienyl]-2-aminobutyryl]amino]-8-oxo-5-thia-1-azabicyclo-[4.2.0]oct-2-ene-2-carboxylic acid |
| 3-[(2-methyl-1,3,4-thiadiazol-5-ylthio)methyl]-7-[[3-[4-(chloromethyl)-phenyl]-2-aminoacetyl]-amino]-8-oxo-5-thia-1-azabicyclo[4.2.0]oct-2-ene-2-carboxylic acid | 3-[(2-methyl-1,3,4-thiadiazol-5-ylthio)methyl]-7-[[2-[4-(pyridiniummethyl)phenyl]-2-aminoacetyl]amino]-8-oxo-5-thia-1-azabicyclo[4.2.0]oct-2-ene-2-carboxylic acid |
| 3-[(1,3,4-thiadiazol-5-ylthio)methyl]-7-[[3-[4-(chloromethyl)phenyl]-2-aminopropionyl]amino]-8-oxo-5-thia-1-azabicyclo[4.2.0]oct-2-ene-2-carboxylic acid | 3-[(1,3,4-thiadiazol-5-ylthio)methyl]-7-[[3-[4-(pyridiniummethyl)phenyl]-2-aminopropionyl]amino]-8-oxo-5-thia-1-azabicyclo-[4.2.0]oct-2-ene-2-carboxylic acid |
| 3-[(3-methyl-1,2,4,-thiadiazol-5-ylthio)methyl]-7-[[4-[4-(chloromethyl)phenoxy]-2-aminobutyryl]amino]-8-oxo-5-thia-1-azabicyclo[4.2.0]oct-2-ene-2-carboxylic acid | 3-[(3-methyl-1,2,4-thiadiazol-5-ylthio)methyl]-7-[[4-[4-(pyridiniummethyl)phenoxy]-2-aminobutyryl]amino]-8-oxo-5-thia-1-azabicyclo[4.2.0]-oct-2-ene-2-carboxylic acid |
| 3-[(tetrazol-5-ylthio)-methyl]7-7[[3-[4-(chloromethyl]phenoxy]-2-aminopropionyl]amino]-8-oxo-5-thia-1-azabicyclo[4.2.0]-oct-2-ene-2-carboxylic acid | 3-[(tetrazol-5-ylthio)-methyl]-7-[[3-[4-(pyridiniummethyl]phenoxy]-2-amino-propionyl]amino]-8-oxo-5-thia-1-azabicyclo[4.2.0]oct-2-ene-2-carboxylic acid |
| 3-[(1-methyltetrazol-5-ylthio)methyl[-7-[[4-[4-(chloromethyl])phenylthio]-2-aminobutyryl]amino]-8-oxo-5-thia-1-azabicyclo-[4.2.0]oct-2-ene-2-carboxylic acid | 3-[(1-methyltetrazol-5-ylthio)methyl]-7-[[4-[4-(pyridiniummethyl)phenylthio]-2-aminobutyryl]amino]-8-oxo-5-thia-1-azabicyclo[4.2.0]-oct-2-ene-2-carboxylic acid |

| CHLOROMETHYL SUBSTITUTED CEPHALOSPORIN DERIVATIVE | PYRIDINIUMMETHYL SUBSTITUTED CEPHALOSPORIN DERIVATIVE |
|---|---|
| 3-[(2-methyl-1,3,4-oxadiazol-5-ylthio)methyl]-7-[[2-[5-(chloromethyl])-2-thienyl]-2-aminoacetyl-amino]-8-oxo-5-thia-1-azabicyclo[4.2.0]oct-2-ene-2-carboxylic acid | 3-[(2-methyl-1,3,4-oxadiazol-5-ylthio)methyl]-7-[[2-[5-(pyridiniummethyl)-2-thienyl-9 -2-aminoacetyl-9 -amino]-8-oxo-5-thia-1-azabityclo[4.2.0]oct-2-ene-2-carboxylic acid |
| 3-[(acetyloxy)methyl]-7-[[2-[4-(chloromethyl)-phenyl]2-aminoacetyl]-amino]-8-oxo-5-thia-1-azabicyclo[4.2.0]oct-2-ene-2-carboxylic acid pivalyloxymethyl ester | 3-[(acetyloxy)methyl]-7-[[2-[4-(pyridiniummethyl)phenyl]-2-aminoacetyl]amino]-8-oxo-5-thia-1-azabicyclo[4.2.0]-oct-2-ene-2-carboxylic acid pivalyloxymethyl ester |
| 3-methyl-7-[[2-[4(chloromethyl)phenyl]-2-aminoacetyl]amino]-8-oxo-5-thia-1-azabicyclo[4.2.0]oct-2-ene-2-carboxylic acid | 3-methyl-7-[[2-[4(pyridiniummethyl)phenyl]-2-aminoacetyl]amino]-8-oxo-5-thia-1-azabicyclo[4.2.0]oct-2-ene-2-carboxylic acid |
| 3-methyl-7-[[2-[4-(chloromethyl)phenyl]-2-aminoacetyl]amino]-8-oxo-5-thia-1-azabicyclo[4.2.0]oct-2-ene-2-carboxylic acid pivalyoxymethyl ester | 3-methyl-7-[[2-[4-(pyridiniummethyl)phenyl[-2-aminoacetyl]amino]-8-oxo-5-thia-1-azabicyclo[4.2.0]oct-2-ene-2-carboxylic acid pivalyloxymethyl ester |

EXAMPLE 28

3-[(Acetyloxy)methyl]-7-[[2-[4-(pyridiniummethyl)-phenyl]-acetyl]amino]-8-oxo-5-thia-1-azabicyclo[4.2.0-]oct-2-ene-2-carboxylic acid N-ethoxycarbonyl-N-methylaminomethyl ester A mixture of 1.2 g of the inner salt of 3-[(acetyloxy)-methyl]-7-[[2-[4-(pyridiniummethyl]phenyl]acetyl]-amino]-8-oxo-5-thia-1-azabicyclo[4.2.0]oct-2-ene-2-carboxylic acid and 0.5 g of N-chloromethyl-N-methylurethane in 40 ml of dimethylformamide is stirred at room temperature for 2 hours. The mixture is poured into ice-water and decanted. The aqueous layer is washed with 75 ml of ethyl acetate filtered and evaporated. The residue is triturated with ether to give 3-[(acetyloxy)methyl]-7-[[2-[4-(pyridiniummethyl)phenyl]acetyl]amino]-8-oxo-5-thia-1-azabicyclo[4.2.0]oct-2-ene-2-carboxylic acid N-ethoxycarbonyl-N-methylaminomethyl ester.

EXAMPLE 29

3-[(Acetyloxy)methyl]-7-[[2-[4-(pyridiniummethyl)-phenyl]-acetyl]amino]-8-oxo-5-thia-1-azabicyclo[4.2.0-]oct-2-ene-2-carboxylic acid p-pivalyloxybenzyl ester To a solution of 1.8 g of 3-[(acetyloxy)methyl]-7-[[2-4-(pyridiniummethyl)phenyl]acetyl]amino]-8-oxo-5-thia-1-azabicyclo[4.2.0]oct-2-ene-2-carboxylic acid hydrochloride in 25 ml of dimethyl formamide is added .78 g of p-pivalyloxybenzyl alcohol followed by cooling to 0° C after which 3.7 mole of dicyclohexylcarbodiimide in 7.5 ml of dimethyl formamide is added dropwise with stirring. The reaction mixture is stirred for 1 hour at 0° C and for an additional 4 hours at room temperature. The formed dicyclohexylurea is removed by filtration. The filtrate is evaporated in vacuo to give an oil which is triturated with ether to give 3-[(acetyloxy)methyl]-7-[[2-[4-(pyridiniummethyl)phenyl]-acetyl]amino]-8-oxo-5-thia-1-azabicyclo[4.2.0]oct-2-ene-2-carboxylic acid p-pivalyloxybenzyl ester.

EXAMPLE 30

3-[(Acetyloxy)methyl]-7-[[2-[4-(pyridiniummethyl)-phenyl]-2-(5-indanyloxycarbonyl)acetyl]amino]-8-oxo-5-thia-1-azabicyclo[4.2.0]oct-2-ene-2-carboxylic acid To 25.3 m mole of 3-[(acetyloxy)methyl]-7-[[2-[4-(pyridiniummethyl)phenyl]-2-catboxyacetyl]amino]-8-oxo-5-thia-1-azabicyclo[4.2.0]oct-2-ene-2-carboxylic acid in 35 ml dioxane is added 6N hydrochloric acid to give a pH of 2.5. Then 24.1 moles N,N'-dicyclohexylcarbodiimide in 35 ml dioxane is added and the mixture is stirred at room temperature for 15 to 20 minutes followed by the addition of 24.1 m moles of 5-indanol. The mixture is stirred for 4 hours. The formed N,N'-dicyclohexylurea is removed by filtration and the filtrate is extracted three times with methyl isobutyl ketone. The organic extract is washed with water, dried over magnesium sulfate and concentrated to dryness in vacuo to yield 3-[(acetyloxy)methyl]-7-[[2-[4-(pyridiniummethyl]phenyl]-2-(5-indanyloxycarbonyl)acetyl]-amino]-8-oxo-5-thia-1-azabicyclo[4.2.0]oct-2-ene-2-carboxylic acid.

EXAMPLE 31 p-Pyridiniummethylphenylacetic acid hydrochloride

A solution of 0.25 g (1.33 mM) of p-chlormethyl-phenylacetic acid and 10 ml of pyridine is refluxed in 65 ml of ethanol for 3½ hours after which the solvent is removed in vacuo at room temperature. The resulting oil is triturated with 110 ml of acetone/benzene [1:2] to give p-pyridiniummethylphenylacetic acid hydrochloride.

In a similar manner, when an appropriate amount of a chloromethyl derivative listed in Table I, Table II and Table III is substituted for p-chlorophenylacetic acid in the above procedure, the corresponding pyridiniummethyl acid derivative is obtained.

EXAMPLE 32

3-[(Acetyloxy)methyl]-7-[[2-[4-(pyridiniummethyl)-phenyl]-acetyl]amino]-8-oxo-5-thia-1-azabicyclo[4.2.0-]oct-2-ene-2-carboxylic acid A mixtue of 1.2 grams of 3-[(acetyloxy)methyl]-7-amino-8-oxo-5-thia-1-azabicyclo[4.2.0]oct-2-ene-2-carboxylic acid and 1.2 grams of p-pyridiniummethylphenylacetic acid chloride HCl in 55 ml of dimethylformamide containing 0.5 ml of triethylamine is stirred for 1½ hours after which the solvent is removed yielding 3-[(acetyloxy)methyl]-7-[[2-[4-(pyridiniummethyl)-phenyl]acetyl]amino]-8-oxo-5-thia-1-azabicyclo[4.2.0-]oct-2-ene-2-carboxylic acid which can be further purified by trituration with chloroform.

In a similar manner as in the above procedure when an appropriate amount of a pyridiniummethyl acid derivative described in Example 31 is substituted for p-pyridiniummethylphenylacetic acid the corresponding pyridiniummethyl substituted cephalosporin derivative is obtained.

EXAMPLE 33

3-(2-Methyl-1,3,4-thiadiazol-5-ylthio)-7-[[2-[4-(pyridiniummethyl)phenyl]acetyl]amino]-8-oxo-5-thia-1-azabicyclo[4.2.0]oct-2-ene-2-carboxylic acid A solution of 3 mM of the inner salt of 3-[(acetyloxymethyl]-7-[[2-[4-(pyridiniummethyl)phenyl]acetyl]amino]-8 -oxo-5-thia-1-azabicyclo[4.2.0]oct-2-carboxylic acid in 100 ml of water is treated with 3 mM of sodium bicarbonate and 6 mM of 2-methyl-1,3,4-thiadiazol-5-yl-thio at 70° C under nitrogen for 3½ hours. The water is removed in vacuo and the residue is triturated with ether then filtered and dried in a vacuum desiccator to give 3-(2-methyl-1,3,4-thiadiazol-5-ylthio)-7-[[2-[4-(pyridiniummethyl)phenyl]acetyl]amino]-8oxo-5-thia-1-azabicyclo[4.2.0]oct-2ene-2-carboxylic acid.

In similar manner other compounds of this invention wherein the 3-position of the cephalosporin molecule is substituted with a heterocyclicthiomethyl group as described in Formula I can be prepared by solvolysis of the corresponding 3-acetoxy derivative with an appropriate heterocyclicthiol compound.

We claim:
1. A compound selected from a base of the formula:

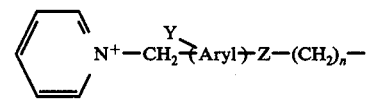

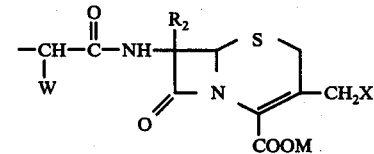

wherein Aryl is selected from phenyl and 2-thienyl; Y is selected from hydrogen, chlorine, bromine, a straight or branched lower alkyl group of from 1 to 4 carbon atoms, and a lower alkoxy group of from 1 to 4 carbon atoms with the proviso that when Aryl is 2-thienyl, Y is hydrogen; Z is selected from a bond, oxygen, sulfur and imino with the proviso that when Aryl is 2-thienyl, Z is a bond; W is selected from hydrogen, methyl, amino, hydroxy, $SO_3H$ and $COOR_1$ wherein $R_1$ is selected from hydrogen and 5-indanyl; n is zero, 1 or 2 with the proviso that when W is other than hydrogen or methyl, and Z is other than a bond, n is not zero; $R_2$ is selected from hydrogen or methoxy and is either cis- or trans-; M is selected from an anion; hydrogen; alkanoyloxymethyl wherein the alkanoyl moiety contains from 1 to 5 carbon atoms and may be straight or branched; alkanoylaminomethyl wherein the alkanoyl moiety contains from 1 to 5 carbon atoms and may be straight or branched and wherein the amino nitrogen may be substituted with an alkyl group of from 1 to 4 carbon atoms; alkoxycarbonylaminomethyl wherein the alkoxy moiety contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; and aminoalkanoyloxymethyl wherein the alkanoyl moiety contains from 2 to 15 carbon atoms, and the amino nitrogen atom may be mono- or di-substituted with a lower alkyl group of from 1 to 4 carbon atoms; with the proviso that when M is other than an anion the compound exists as a salt of a pharmaceutically acceptable inorganic or organic acid; X is selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5ylthio and 1,2,3-triazol-5-ylthio; and pharmaceutically acceptable salts thereof.

2. A compound of claim 1 wherein Aryl is phenyl.
3. A compound of claim 2 wherein the $R_2$ substituent is in the cis-position.
4. A compound of claim 1 wherein Aryl is 2-thienyl.
5. A compound of claim 4 wherein the $R_2$ substituent is in the cis-position.
6. A compound of claim 1 wherein W is hydrogen.
7. A compound of claim 6 wherein Z is a bond.
8. A compound of claim 6 wherein Z is oxygen or sulfur.
9. A compound of claim 6 wherein Z is imino.
10. A compound of claim 1 wherein W is methyl.
11. A compound of claim 10 wherein Z is a bond.
12. A compound of claim 10 wherein Z is oxygen or sulfur.
13. A compound of claim 10 wherein Z is imino.
14. A compound of claim 1 wherein W is hydroxy.
15. A compound of claim 14 wherein Z is a bond.
16. A compound of claim 14 wherein Z is oxygen or sulfur.
17. A compound of claim 14 wherein Z is imino.
18. A compound of claim 1 wherein W is amino.
19. A compound of claim 18 wherein Z is a bond.
20. A compound of claim 18 wherein Z is oxygen or sulfur.
21. A compound of claim 18 wherein Z is imino.
22. A compound of claim 1 wherein W is $COOR_4$ or $SO_3H$.
23. A compound of claim 22 wherein Z is a bond.
24. A compound of claim 22 wherein Z is oxygen or sulfur.
25. A compound of claim 22 wherein Z is imino.
26. A compound selected from a base of the formula:

28. A compound of claim 26 which is 3-[(1-methyltetrazol-5-ylthio)methyl]-7-[[2-[4-(pyridiniummethyl)-phenyl]acetyl]amino]-8-oxo-5-thia-1-azabicyclo[4.2.0]-oct-2-ene-2-carboxylic acid and pharmaceutically acceptable salts thereof.
29. A compound of claim 26 which is 3-[(2-methyl-1,2,4-thiadiazol-5-ylthio)methyl]-7-[[2-[4-(pyridiniummethyl)phenyl]-2-hydroxyacetyl]amino]-8-oxo-5-thia-1-azabicyclo[4.2.0]oct-2-ene-2-carboxylic acid and pharmaceutically acceptable salts thereof.
30. A compound of claim 26 which is 3-[(1-methyltetrazol-5-ylthio)methyl[-7-[[2-[4-(pyridiniummethyl)-phenyl]-2-hydroxy-acetyl]amino]-8-oxo-5-thia-1-azabicyclo[4.2.0]oct-2-ene-2-carboxylic acid and pharmaceutically acceptable salts thereof.
31. A compound of claim 26 which is 3-[(2-methyl-1,2,4-thiadiazol-5-ylthio)methyl]-7-[[2-[4-(pyridiniummethyl)phenyl]-2-aminoacetyl]amino]-8-oxo-5-thia-1-azabicyclo[4.2.0]oct-2-ene-2-carboxylic acid and pharmaceutically acceptable salts thereof.
32. A compound of claim 26 which is 3-[(1-methyltetrazol-5-ylthio)methyl]-7-[[2-[4-(pyridiniummethyl)-phenyl]-2-amino-acetyl]amino]-8-oxo-5-thia-1-azabicyclo[4.2.0]oct-2-ene-2-carboxylic acid and pharmaceutically acceptable salts thereof.
33. A compound of claim 26 which is 3-[(2-methyl-1,2,4-thiadiazol-5-ylthio)methyl]-7-[[2-[4-(pyridiniummethyl)phenyl]-2-carboxyacetyl]amino]-8-oxo-5-thia-1-azabicyclo[4.2.0]oct-2-ene-2-carboxylic acid and pharmaceutically acceptable salts thereof.
34. A compound of claim 26 which is 3-[(1-methyltetrazol-5-ylthio)methyl]-7-[[2-[4-pyridiniummethyl)-phenyl]-2-carboxy-acetyl]amino]-8-oxo-5-thia-1-azabicyclo[4.2.0]oct-2-ene-2-carboxylic acid and pharmaceutically acceptable salts thereof.
35. A compound of claim 26 which is 3-[(2-methyl-1,2,4-thiadiazol-5-ylthio)methyl]-7-[[2-[4-(pyridiniummethyl)phenyl]-2-sulfoacetyl]amino]-8-oxo-5-thia-1-azabicyclo[4.2.0]oct-2-ene-2-carboxylic acid and pharmaceutically acceptable salts thereof.

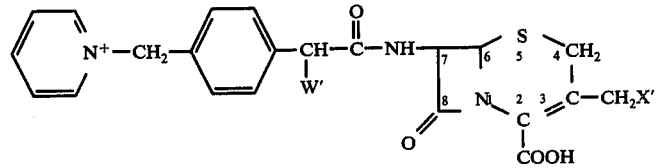

wherein W' is selected from hydrogen, hydroxy, amino, COOH, or $SO_3H$; X' is selected from 3-methyl-1,2,4-thiadiazol-5-ylthio, and 1-methyltetrazol-5-ylthio; and wherein the hydrogen atoms at the 6- and 7-positions are cis to one another; and pharmaceutically acceptable salts thereof.

27. A compound of claim 26 which is 3-[(2-methyl-1,2,4-thiadiazol-5-ylthio)methyl]-7-[[2-[4-(pyridinium- 36. A compound of claim 26 which is 3-[(1-methyltetrazol-5-ylthio)methyl]-7-[[2-[4-(pyridiniummethyl)-phenyl]-2-sulfoacetyl]-amino]-8-oxo-5-thia-1-azabicyclo[4.2.0]oct-2-ene-2-carboxylic acid and pharmaceutically acceptable salts thereof.

* * * * *